United States Patent
Van Zuylen et al.

(10) Patent No.: US 6,221,095 B1
(45) Date of Patent: Apr. 24, 2001

(54) METHOD AND APPARATUS FOR PHOTON THERAPY

(75) Inventors: Jeffrey Van Zuylen, Mississauga; Fred Kahn, Toronto; Iain Campbell, Owen Sound; Christopher L. M. Stoute, North York, all of (CA)

(73) Assignee: Meditech International Inc., Toronto (CA)

( * ) Notice: Subject to any disclaimer, the term of this patent is extended or adjusted under 35 U.S.C. 154(b) by 0 days.

(21) Appl. No.: 08/892,857

(22) Filed: Jul. 15, 1997

(30) Foreign Application Priority Data

Nov. 13, 1999 (GB) .................................................. 9623627

(51) Int. Cl.[7] ..................................................... A61N 1/18
(52) U.S. Cl. ................................. 607/88; 607/89; 606/15; 606/9
(58) Field of Search ........................ 607/88–92; 606/13, 606/15, 9

(56) References Cited

U.S. PATENT DOCUMENTS

| | | |
|---|---|---|
| 4,279,254 * | 7/1981 | Boschetti et al. . |
| 4,819,646 * | 4/1989 | Cheung et al. ...................... 600/323 |
| 4,930,504 | 6/1990 | Daimontopoulos et al. . |
| 5,050,597 | 9/1991 | Daikuzono . |
| 5,240,417 | 8/1993 | Smithson . |
| 5,259,380 | 11/1993 | Mendes et al. . |
| 5,337,741 | 8/1994 | Diamond . |
| 5,358,503 | 10/1994 | Burtwelll et al. . |
| 5,383,208 * | 1/1995 | Queniat et al. ......................... 372/29 |
| 5,383,874 * | 1/1995 | Jackson et al. ........................... 606/1 |
| 5,401,270 | 3/1995 | Muller et al. . |
| 5,409,482 | 4/1995 | Diamontopoulos . |
| 5,474,528 * | 12/1995 | Meserol ................................. 604/20 |
| 5,683,436 * | 11/1997 | Mendes et al. ......................... 607/88 |
| 5,698,866 * | 12/1997 | Doiron et al. .......................... 257/99 |
| 5,728,090 * | 3/1998 | Martin et al. ............................ 606/3 |
| 5,734,668 * | 3/1998 | Raven et al. ........................... 372/38 |
| 5,755,752 * | 5/1998 | Segal ..................................... 607/89 |
| 5,783,909 * | 7/1998 | Hochstein ............................. 315/159 |

* cited by examiner

Primary Examiner—Linda C. M. Dvorak
Assistant Examiner—Roy Gibson
(74) Attorney, Agent, or Firm—Ladas & Parry

(57) ABSTRACT

A photon therapy unit implement has a flexible head for conforming to a body part to be treated. The head has a thermally conductive backing to remove heat form the treatment area. The operation of the head is monitored by a photon detector to provide a feedback to the diode drive circuit to maintain the output at the required level. Operation of the head is monitored by a microprocessor which performs a diagnostic function and reports on defects. The treatment protocol is generated by a main control unit that formulates a treatment waveform from a set of treatment protocols. The selection of protocols is performed through a graphical user interface (GUI) which allows selection of treatment areas and customization of treatment as well as maintaining patient history and annotations.

25 Claims, 39 Drawing Sheets

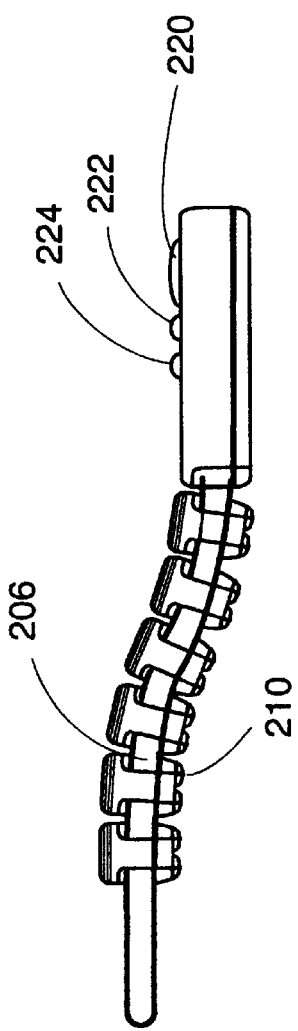
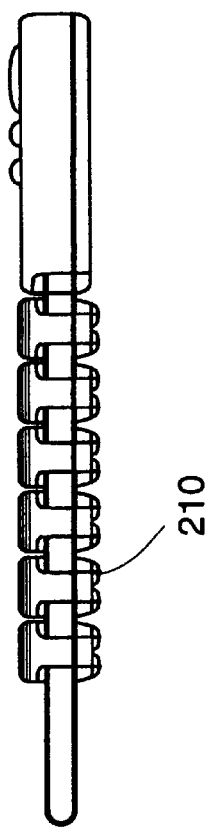
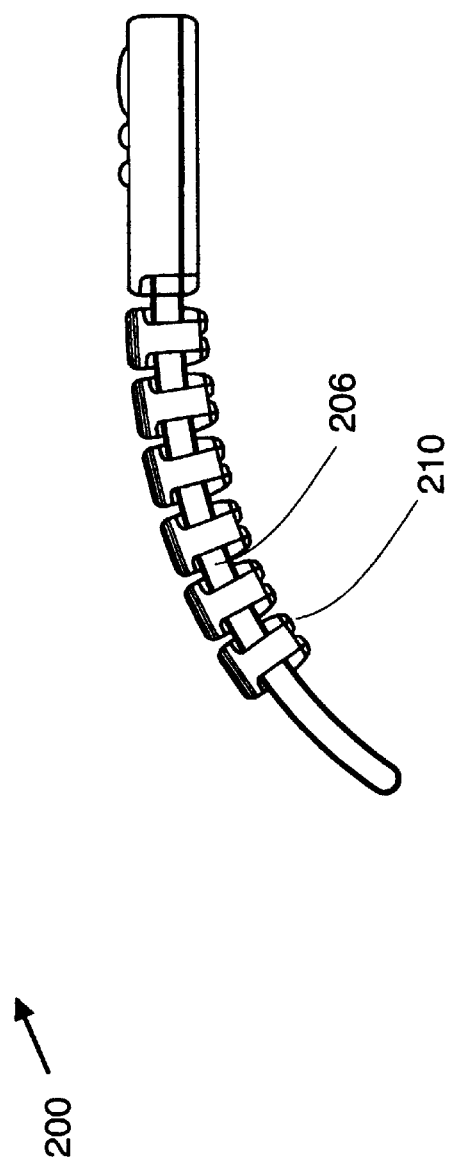
Figure 5 a
Figure 5 b
Figure 5 c

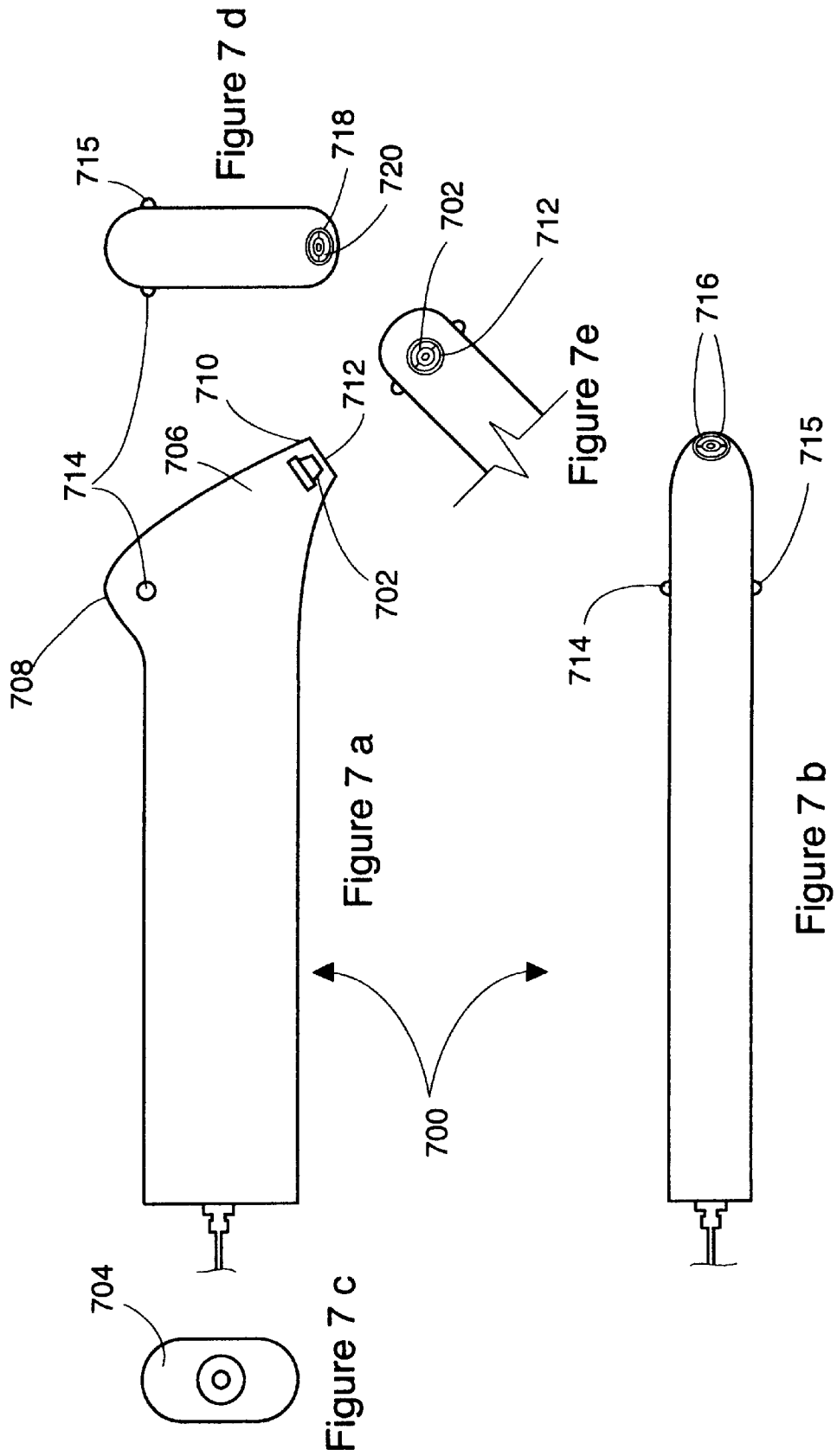

Figure 22 (a)

New Patient
Both name and code number must be entered:
Name:
Code number:
Factors
Date of Birth   Jan. 1 ,1960
Accept   Reject   Help

Figure 22 (b)

Select Existing Patient
Select patient by code number:
Select by:
⦿ name
○ code

Apu
Bart Simpson
Crusty the Clown
Homer Simpson
Ken Jones
Lisa Simpson
Maggie Simpson
Marge Simpson
Seymour Skinner Accept
Reject
Delete patient
Help

Figure 22 (c)

Patient Factors
Age
○ Juvenille
⦿ Adult
○ Senior

Complexion
⦿ Caucasian
○ Asian
○ African

Build
○ Ectomorph
⦿ Mesomorph
○ Endomorph

Accept
Reject
Help

Create Prescription                                    ☒

| Repeat treatment every: | 2 | days | Accept | Reject |
| Total number of treatments: | 3 | | | |
| Number of stages in treatment: | 1 | | Help | |

Stage Details

Calculate | Stage: 1
Stage ends with: end of treatment

Head type
LS-R250  ▽ | Head details

Parameters of operation

| Average power: | 83 | mW |
| Peak power: | 250.0 | mW |
| Percent power: | 100 | %max |
| Spot size/Area: | 24.000 | cm$^2$ |
| Power density: | 3.4 | mW/cm$^2$ |
| Duration: | 2 | s |
| Energy density: | 0.006 | J/cm$^2$ |
| Time on: | 5000 | ps |
| Time off: | 10000 | ps |

Mode of operation
- ○ Continuous wave
- ○ Modulation
- ⦿ Pulsed

Figure 25 (b)

Head Parameters                                    ☒

Head type: LS-R250
Version: V1.0                                    Close | Help Laser class: 11.lb            Total optical power: 250 mW
Array type: multi             Total surface area: 24.000 cm$^2$
Source count: 1               Irradiance: 10.4 mW/cm$^2$

Source Details

Source number: 1

| Device Count: 60 | Wavelength: 660 nm |
| Medium: GaAlAs | Spectral width: 25.0 nm |
| Type: LED | Divergence: 8.8 deg |
| Coherance length: 0 mm | Device power: 4.2 mW |

Figure 27

| Create Prescription | | | | | ☒ |
|---|---|---|---|---|---|
| Repeat treatment every: | 2 | days | Accept | | Reject |
| Total number of treatments: | 3 | | | | |
| Number of stages in treatment: | 1 | | Help | | |

Stage Details

[Calculate] Stage: 1
Stage ends with: end of treatment

Head type: LD-130 ▽   Head details...

Parameters of operation
Average power:      30.0    mW
Percent power:      100     %max
Spot size/Area:     0.010   $cm^2$
Power density:      3000.0  $mW/cm^2$
Duration:           2       s
Energy density:     6.000   $J/cm^2$ Mode of operation
⦿ Continuous wave
○ Modulation
○ Pulsed

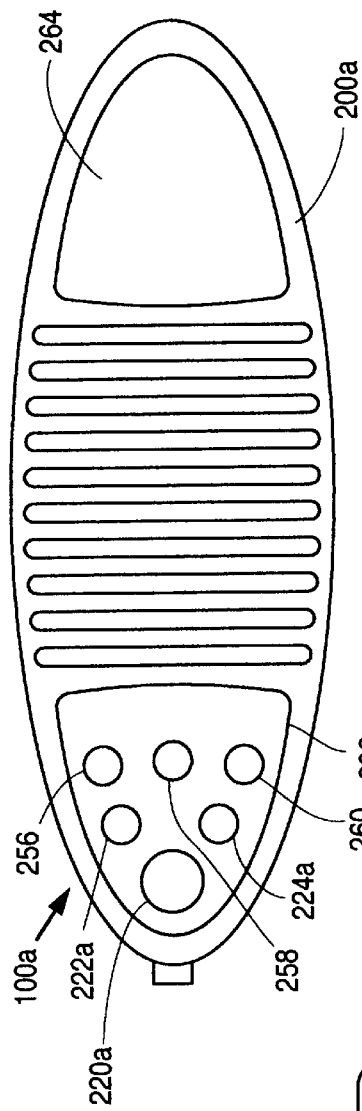
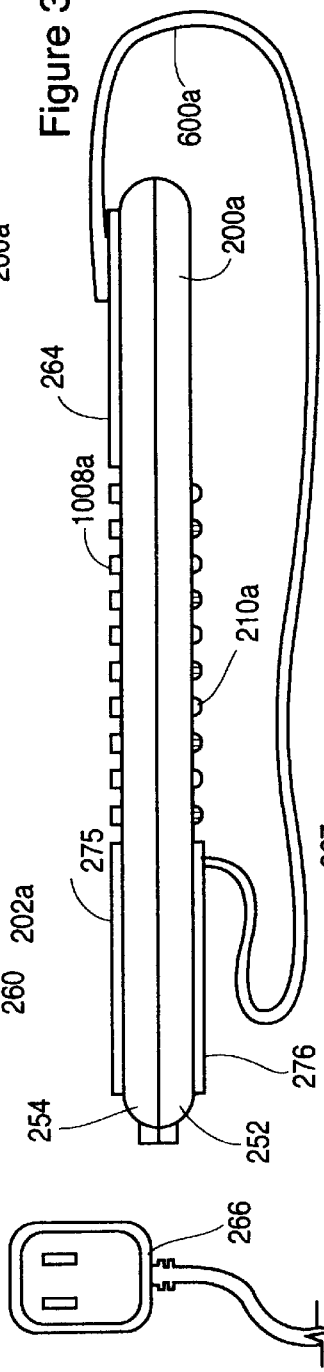
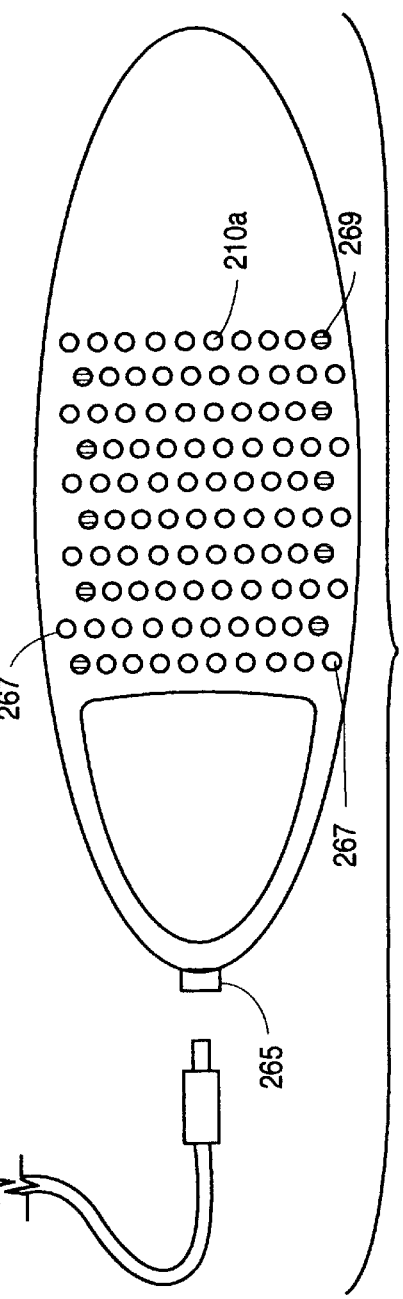
Figure 33
Figure 34
Figure 35

METHOD AND APPARATUS FOR PHOTON THERAPY

This invention relates to a photon therapy system, commonly referred to as a low intensity laser therapy system, wherein a substantial number of treatment parameters may be relatively accurately and consistently controlled.

BACKGROUND OF THE INVENTION

1. Field of the Invention

Photon therapy is used amongst others for the treatment of muscular skeletal disorders and wound healing. Photon therapy systems are primarily administered by chiropractors, physiotherapists, sports therapists, and medical doctors in a clinical environment. Generally, photon therapy treatment is effected by applying light energy or photons in the visible and/or infrared regions to parts of the body. Strictly speaking, in photon therapy the light energy generated does not produce any significant heating effects but does invoke photochemical and photobiolgical effects in the biological tissue.

2. Description of the Prior Art

While numerous photon therapy systems are in existence today, non provide a complete range of flexiblility in choosing treatment parameters. Having the ability to choose various treatment parameters is essential for a commercial application. For example, U.S. Pat. No. 5,358,503 to Bertwell et al. describes a flexible pad in which an array of photodiodes are mounted. Power is supplied to the pads and is controlled by a knob connected to a rheostat. A current supplied to the pads is visually monitored by a light bar display. One of the major disadvantages of this device is the inability to guarantee consistent priorities for successive treatments. Although the patent describes a mechanism for recording treatments applied to specific body regions, there is no guarantee that with this device the amount of current supplied to the pads as set by the rheostat will always produce the same light intensity from the diodes on successive treatments.

U.S. Pat No. 5,259,380 to Mendes et al. discloses a light therapy system in which the light is emitted in a narrow bandwidth. A continuous voltage differential is utilized to energize the diodes.

In U.S. Pat. No. 4,930,504, a device for biostimulation of tissue is disclosed which comprises an array of substantially monochromatic radiation sources of at least three different wavelengths. The system has a control unit to which a single beam probe or a cluster beam probe may be connected. The control unit provides control of the beam radiation pulse frequency, duration, period of treatment and measurement of the conductivity of the tissue being treated. A means for measuring the optical power emitted by the probes is described.

As mentioned briefly above, of the numerous photon therapy systems in existence, none provide the ability to accurately vary the pulse width, duty cycle, waveform, average power and peak power as well as provide a "hands off" treatment of the practitioner. Furthermore, the probes of the prior art do not provide internal diagnostics.

SUMMARY OF THE INVENTION

This invention seeks to provide an apparatus for photon therapy in which treatments may be completely, accurately and consistently characterized.

BRIEF DESCRIPTION OF THE DRAWINGS

Embodiments of the invention will now be described by way of example only with reference to the detailed description below and in connection with the following drawings, in which

FIGS. 5(a)–(c) show a tip, side and bottom view respectively of a flexible treatment head;

FIGS. 7(a) –(h) show various vies of a second embodiment of head in which

FIG. 7(a) is a side view of the head,

FIG. 7(b) is a plan view of FIG. 7a,

FIG. 7(c) is a rear view of FIG. 7(a),

FIG. 7(d) is a front view of the head of FIG. 7(a),

FIG. 7(e) is a view in the direction of arrow e—e of FIG. 7(a),

FIG. 7(f) is an enlarged perspective view of a component used in the head shown in FIG. 7(a), FIG. 7(g) is a side view of the component of FIG. 7(f), and FIG. 7(h) is an end view of the component of FIG. 7(f);

FIG. 33 is a plan view of a further embodiment of treatment head;

FIG. 34 is a side view of the treatment head of FIG. 33;

FIG. 35 is a bottom view of the underside of the treatment head of FIG. 33;

DESCRIPTION OF THE PREFERRED EMBODIMENTS OF TREATMENT HEAD

Figure 1:
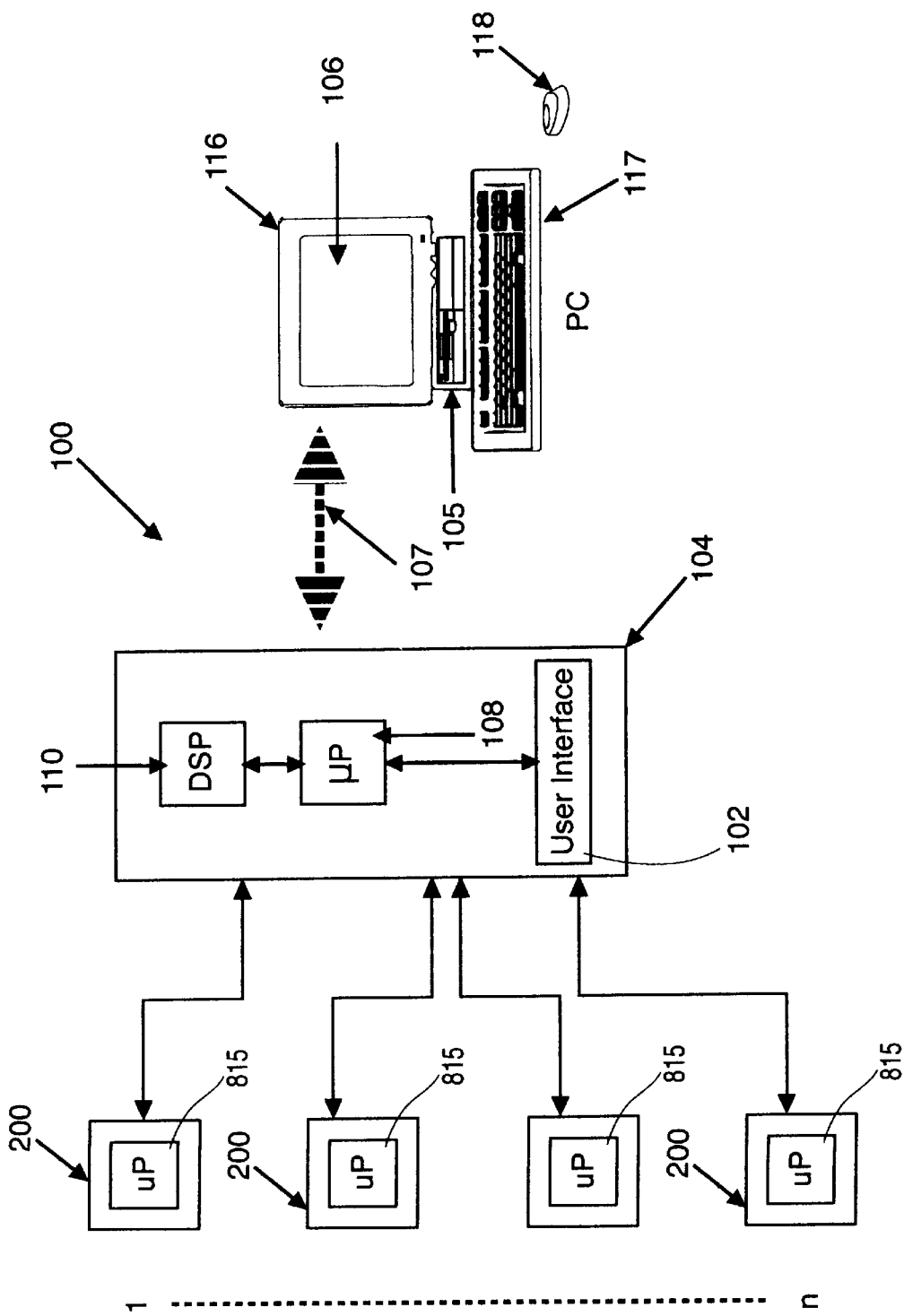
FIG. 1 is a block diagram of the overall system architecture.

Referring to FIG. 1, the various components of a photon therapy system are shown generally by numeral 100. The system is composed of three main components, namely one or more treatment heads 200, a main controller (MCU) 104 and a computer 105 for running a graphical user interface program 106 and including a display 116, keyboard 117 and mouse 118. The computer 105 communicates with the MCU 104 via an RS232 link 107, while the treatment heads 200 are connected via a suitable cable to the main controller 104. Communication between each of the components 105,104 and 200 is achieved by using a specific protocol. Details of these protocols will be discussed later. As an overview, the treatment heads 200 generate and deliver light energy to the anatomical area requiring treatment. The treatment heads 200 may have specific key operating characteristics, including coherence, spectral width, peak operating wavelength, maximum irradiance and beam profile stored within dedicated microprocessors 815 in each had 200. The system 100 is preferably capable of recognizing and utilizing multiple treatment heads 200 with varying characteristics by communicating with the dedicated microprocessors 815. The light energy sources used in the treatment heads 200 may include semiconductor laser diodes (LD) and superluminous diodes (SLD) also known as light-emitting diodes (LED).

The main controller unit 104 is composed of two major components, a microprocessor 108 and a digital signal processor (DSP) 110. The microprocessor 108 is responsible for the overall system operation while the DSP 110 is responsible for producing complex treatment protocols and for performing complex calculations under the direction of microprocessor 108. Treatment protocols are a series of operating parameters which control the treatment heads 200 and include control of such diode parameters as frequency, duty cycle, wave form, average power and peak power. MCU 104 is also provided with a standalone user interface 102 when GUI 106 is not available.

The graphical user interface (GUI) 106 is a software system that resides in memory on the computer 105 and serves to control the MCU 104 via information exchanged along the RS232 link 107. The GUI includes a database of preset prescription protocols, patient record-keeping, anatomical illustrations, detail specifications, customized treatments and the like. Each of the system components will now be discussed in detail below.

Figure 7H:
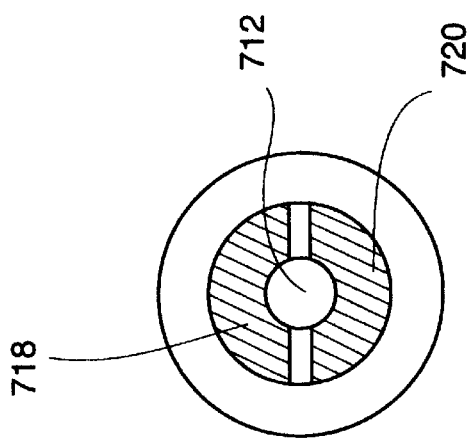
Figure 7G:
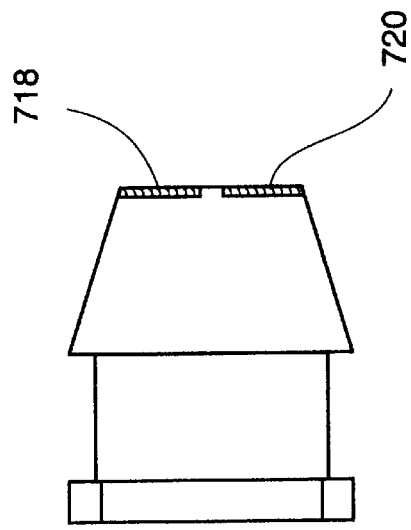
Figure 7F:
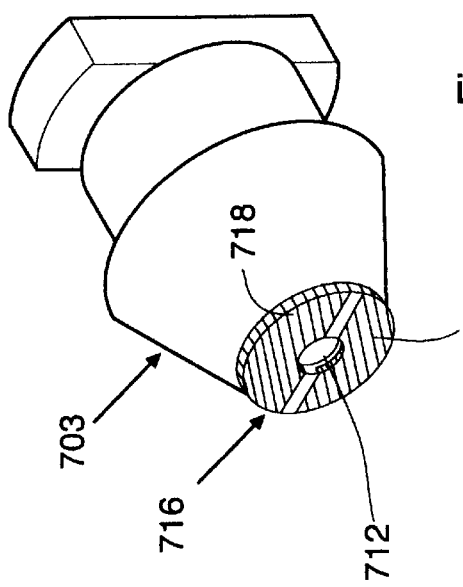
Figure 36:
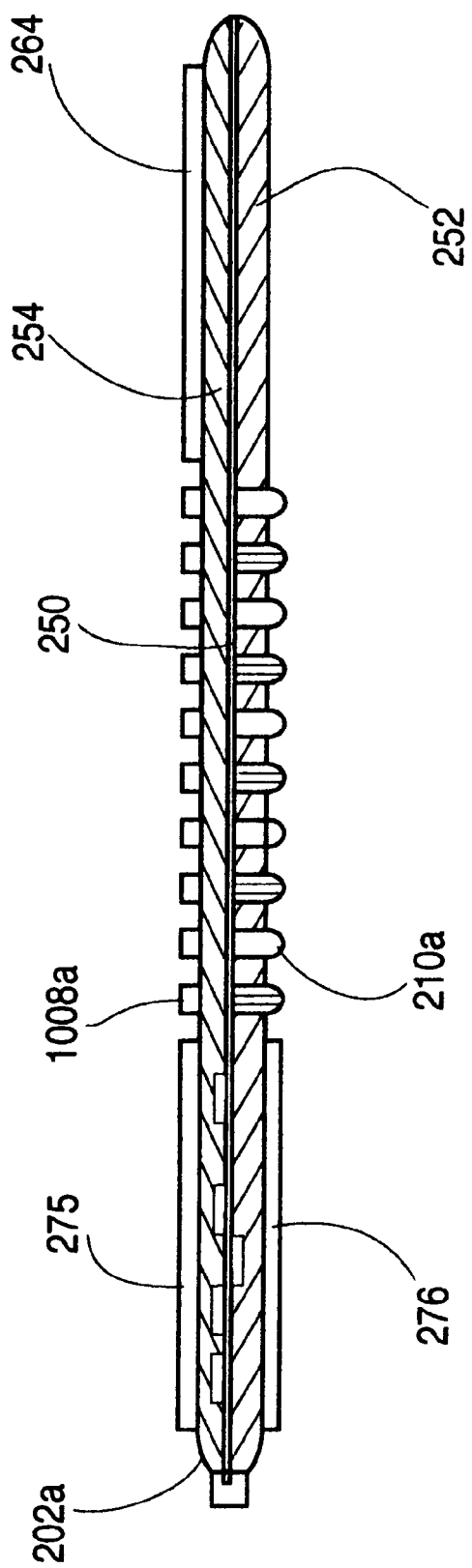
FIG. 36 is a sectional view on the line 36—36 of FIG. 33.

Several types of treatment heads are described in the following description. FIGS. 2(a), 2(b), 2(c), 3, 4 and 5(a)–(c) illustrate a flexible treatment head shown generally by numeral 200 primarily for treating large surface areas, while FIG. 7 illustrates a single source treatment head 700 generally referred to as a laser treatment head, which may be used for the treatment of numerous smaller regions or for stimulating acupuncture points. FIGS. 33–35 show a further embodiment of treatment head intended for personal use and FIG. 36 shows ahead similar to FIGS. 33–35 with an enhanced interface.

Figure 6:
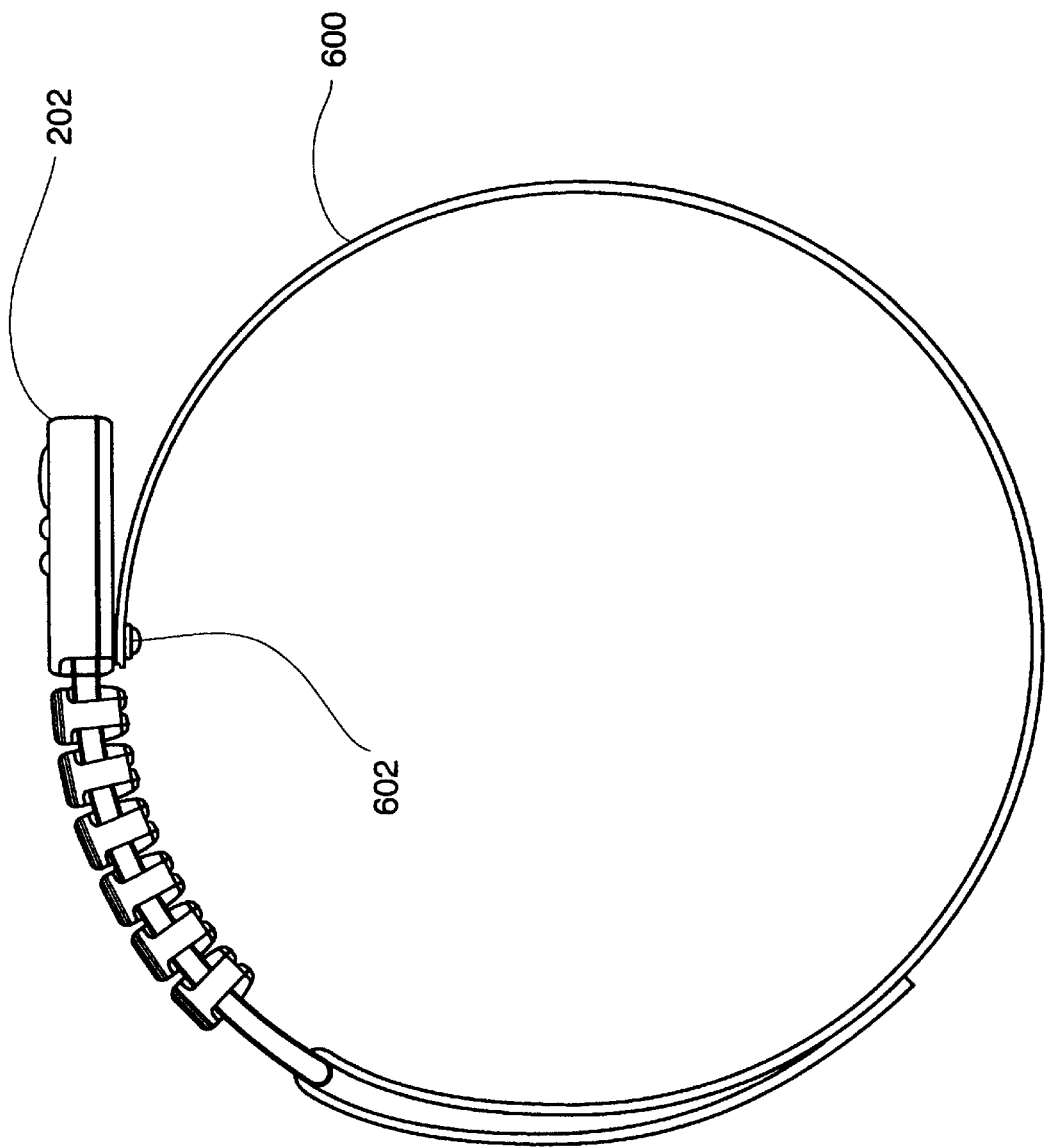
FIG. 6 shows a side view of the flexible treatment head which includes an attachment strap.

In FIGS. 2(a)–(c), in which like numerals indicate similar structures, a flexible head is shown generally by numeral 200. The flexible head 200 includes a rectangular control pod 202 or housing which contains the main circuitry for controlling and powering diodes 210; and a plurality of diode carrying pockets 204 extending from one end of the control pod and threaded on a flexible tubing 206. The flexible tubing 206 is arranged to form a loop 208 at the end of the treatment head 200. The loop 208 serves as a means for grasping and manipulating the flexible head 200 or for attaching a flexible strap such as a Velcro strap 600 as shown in FIG. 6. Preferably in this arrangement, the VELCRO attachment strap 600 is attached at one end 602 to the underside of the pod 202 adjacent the first of the pockets 204. The strap mechanism allows the flexible head to be attached to a patient, thus providing for a so-called "hands-off" treatment of a patient by a practitioner without flexing the pod 202. The control pod 202 includes the main circuitry for controlling and powering the diodes.

Figure 4:
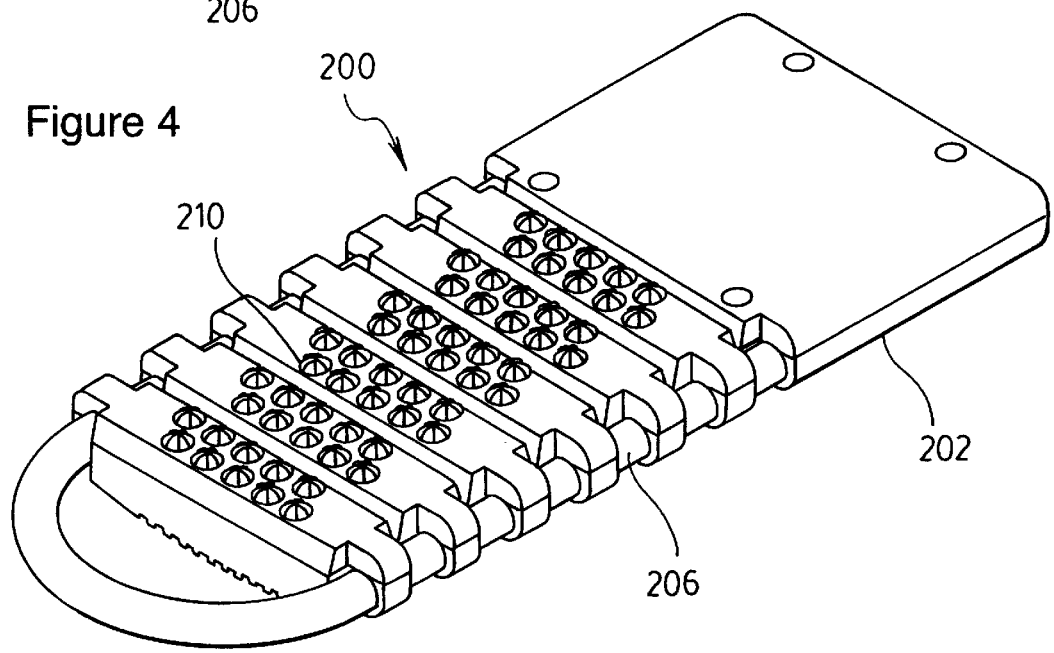
FIG. 4 shows a perspective view of the bottom of the flexible treatment head.

The diodes 210 project from a bottom surface of the treatment head 200 as more clearly seen in FIGS. 2(b) and FIG. 4. Each pocket 204 as shown in the embodiment contains an array of diode devices 210. In the preferred embodiment, the diode devices are SLD devices. Each array of the SLDs is arranged in two linear rows 290 and 292 of five diodes each. Adjacent linear rows of diodes are staggered in order to achieve a closer packing density as well as to provide an increased luminous output per unit area. This arrangement also enables the pockets to be made relatively narrow, which when arranged side by side on the flexible tubing, allow a high degree of flexibility as shown in figures 5(a), (b) and (c), thus allowing the head to easily conform to various parts of the body being treated in order to provide good coupling of light energy to the treatment area.

In the embodiment shown, 10 diodes are used in each array, which to some extend is dictated by supply voltage, forward voltage drop of the diodes and its available driver circuitry. In this embodiment, this provides a surface area of approximately 24 square centimetres. However, a larger or lesser number of diodes may be utilized, in order to realize a correspondingly larger or smaller head. For example, in another embodiment, the flexible head may contain 20 SLD's per pocket with a total of eight pockets resulting in a surface area of approximately 65 square centimeters.

Figure 10:
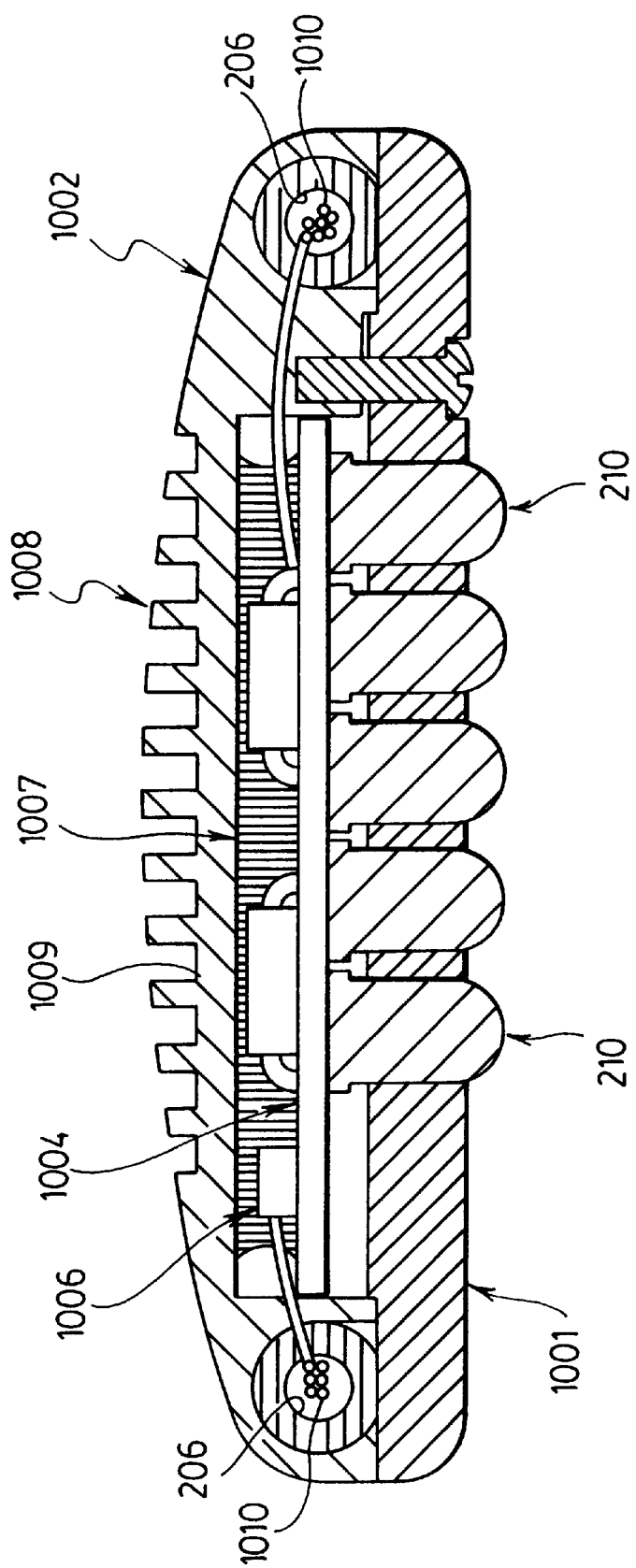
FIG. 10 shows a cross-sectional view of the diode pod.

Referring to FIG. 10, a cross-sectional view of a pocket 204 is shown. As may be seen, the SLDs 210 are mounted on one side of a printed circuit board 1004 and arranged to project from one side of the pocket 204 on the lower surface of the treatment head 200. Each pocket includes a driver 1006 for controlling power to the diodes 210 of that array and in the preferred embodiment comprise a FET and a resistor. One of the problems associated with treatment head in general is the generation of heat from the diode devices 210. This is particularly problematic with a large number of devices. Photon therapy by definition should not produce any substantial increase in skin surface temperature. In order to minimize the heating effect of the diodes 210 and the driver 1006, the bottom surface 1001 of the pockets 1000 comprise a thermally insulating plastics material, while the upper surface 1002 comprises an aluminum heat sink 1009. Internally the diodes 210, driver 1006 and PCB 1004 are thermally connected to the aluminum heat sink 1009 by thermal epoxy 1007, providing heat transfer from the inside of the pocket to the outside tip surface of the pocket. The upper surface of the aluminum heat sink is grooved to form cooling fins 1008. Furthermore the surface of the aluminium is painted black in order to increase its emisivity. Thus both radiation and convection are optimized to reduce the temperature of the head surface 1001 which is in contact with the patient. Power to the driver 1006 is supplied by a conductor 1010 located within the tube 206. Power in the conductor is controlled by the circuitry in the pod 202.

Figure 11:
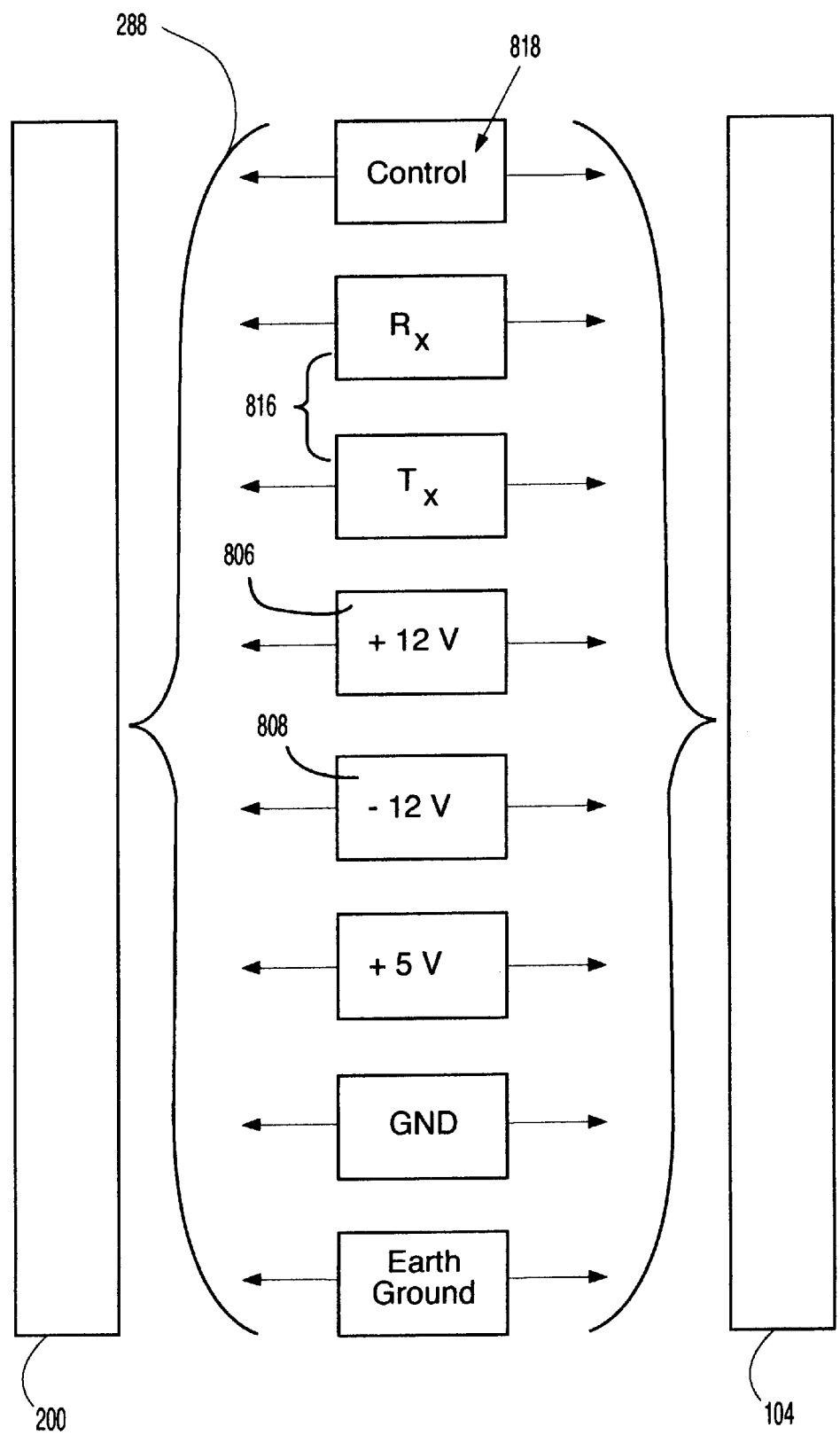
FIG. 11 shows the control signals between the main controller and a treatment head.

Referring back to FIGS. 2(a)–(c), a flexible control cable 288 extends from an opposite end of the pod 202 and connects the treatment head 202 to the main control unit 104 via a suitable connector. As may be seen in FIG. 11, in addition to ground and power signals, an RS-232 Tx and Rx line and a control voltage line 818 is provided from the MCU 104 via the main control cable 288. Power to the drive 1006 of each of the pockets is derived from the circuitry in the pod 202 and is fed via the conductors in the flexible cable 206 to each of the pockets 204.

Figure 8:
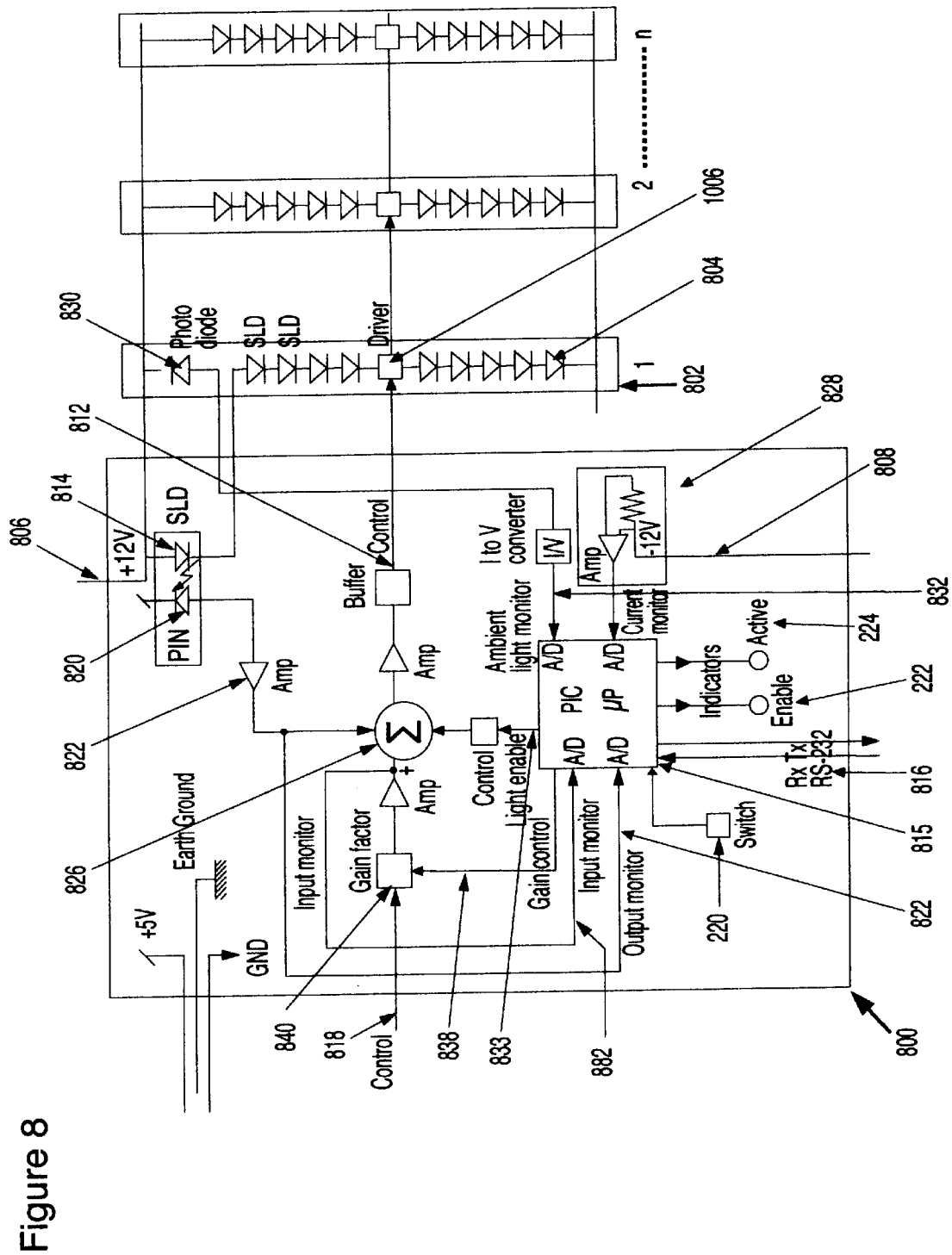
FIG. 8 is a schematic block diagram of the electrical control circuit for the flexible head.

Referring to FIG. 8, a schematic block diagram of the control circuitry associated with the pod 202 is shown generally by block 800. As shown, the diode devices 210 in each of the pockets 204 are connected in series. In the embodiment shown, this is a string of ten diodes 210, with the string of diodes in successive pockets 204 being connected in parallel. A +12 Volt and −12 Volt supply 806 and 808, respectively, is provided across each string of diodes. A voltage drive signal 812 derived from the control signal 818 in cable 288 is applied to each of FET drivers 1006. The FET drivers are in series with the string of diodes 210 in respective pockets and serves to control the current through the diodes, thus controlling the diode luminosity, in response to the drive signal 812

As stated earlier, a plurality of pockets may be connected together in parallel. In order to ensure that a predictable and consistent luminous signal is provided by the treatment heads 200, a feedback loop was implemented. This is achieved in principle by monitoring the luminous output form one of the diodes in the string. The assumption is that by constructing or ensuring that the remaining strings of diodes in the other pockets behave in a similar manner to the pocket used in the feedback loop, a more consistent luminous output can be achieved.

As shown in FIG. 8, the feedback diode 814 is optically coupled to a pin diode 820, which is responsive to the photon energy generated by the diode 814. The output from the pin diode is fed via an amplifier 822 to an analog to digital input 824 of a microprocessor 815. The microprocessor 815 performs a comparison with this input and with the input from the control signal which is received on the analog it digital input 824. The output from the pin diode 820 and the input from the control signal 818 are compared in a summer 826 to provide the output control signal 812 for the device drivers 810. As may be seen then, the feedback loop around the pin diode 820 and the summer 826 provides a real-time loop with high bandwidth (1 MHz) and thus provides stable and absolute luminous output power that is not dependent upon the type of modulation or the underlying limitation of the diodes. The benefits of this feedback are invaluable in that, for example, if a treatment had is composed of a number of SLD devices—for example 60—but one of the 60 is used to provide feedback as a representative sample, then based on the assumption that the remaining 59 devices will behave in a similar fashion, the effects due to diverse linearity, heating and aging effects are all but eliminated. A further significance of monitoring the luminous output directly in this type of feedback arrangement is that it achieves a direct control of the luminous output rather than the drive current. A pin diode is preferably used as a photo receptor as it provides a linear response while being relatively temperature-insensitive, extremely fast and accepts a wide range of power and spectral intensities.

A further advantage of this feedback arrangement is that the feedback loop integrity may be ensured by utilizing the microprocessor 815 to constantly measure or compare the desired output signal with the measured output signal. These signal lines are indicated as numerals 824 and 822 respectively. Should the signals be dissimilar, the software contained within the microprocessor would inform the main control unit via the RS232 line.

The total current through the diodes 210 is monitored by a current monitor indicated by block 828, which provides a signal on an analogue-to-digital input line of the microprocessor 815. The microprocessor utilized in this embodiment is a PIC16 C71 chip which includes 4 analogue-to-digital input lines. Thus, by monitoring the total current through the diodes 210, a failure of one or more diodes will be noted by a change in total current and once again the microprocessor will communicate this via the RS232 line to the main controller unit. Also, as devices age, more current will be required to maintain a desired intensity; thus a current monitor may inform the user when the useful lifetime of a head has been realized. Thus, the net effect of the feedback loop combined with the built-in diagnostics in the microprocessor 815 ensures a stable, absolute and reliable luminous output.

A photo diode 830 located within a pocket 802 is connected via a current-to-voltage converter to an analogue-to-digital input 832 of the microprocessor in order to provide a signal indicative of the ambient light. The microprocessor 815 receives this ambient light monitor signal 832, relays the information to the MCU over communication lines 816, which determines whether a treatment should be activated. If the head 200 is not attached to a physical object, such as the body, the ambient light reading will be high, indicating an unsafe operating condition. When attached, the ambient light reading will be low and the treatment may proceed. In addition, a user may alter the sensitivity of the ambient light sensor via the GUI software program in order to accommodate various lighting conditions. In addition to communication over control 816, the microprocessor 815 provides a light enable/disable control signal 833 to the summer 826 to ensure that the luminous output is disabled for all situations other than when a treatment is active. This is particularly useful in failsafeing the system and preventing any low-level optical signals from being emitted when the heads are idle. This feature is of particular relevance for laser heads as they operate within the active lasing region and thus low-level or off-power setting is not zero but a relatively low intensity signal compared to the high-level.

Besides performing control functions within the head 200, the microprocessor 815 stores an identification of the head 200 and its operating characteristics that it may communication to the MCU 104 over lines 816.

SLD devices 210 are capable of producing high instantaneous optical peak power pulses, often an order of magnitude greater than its average optical power output. These high instantaneous peak pulses may be produced if the pulses are of short duration and duty cycle (typically 10 microseconds, 15DC). To provide a suitable form of control signal for SLDs 210, a fixed gain amplifier 840 is provided between the control signal line 818 and the summer 826 and is controlled from the microprocessor 815 via gain control line 838. Thus, when the gain amplifier 840 is activated, the signal to the driver is amplified by a predetermined factor, amplifying the light output by a corresponding factor as will be explained more fully below.

Figure 2:
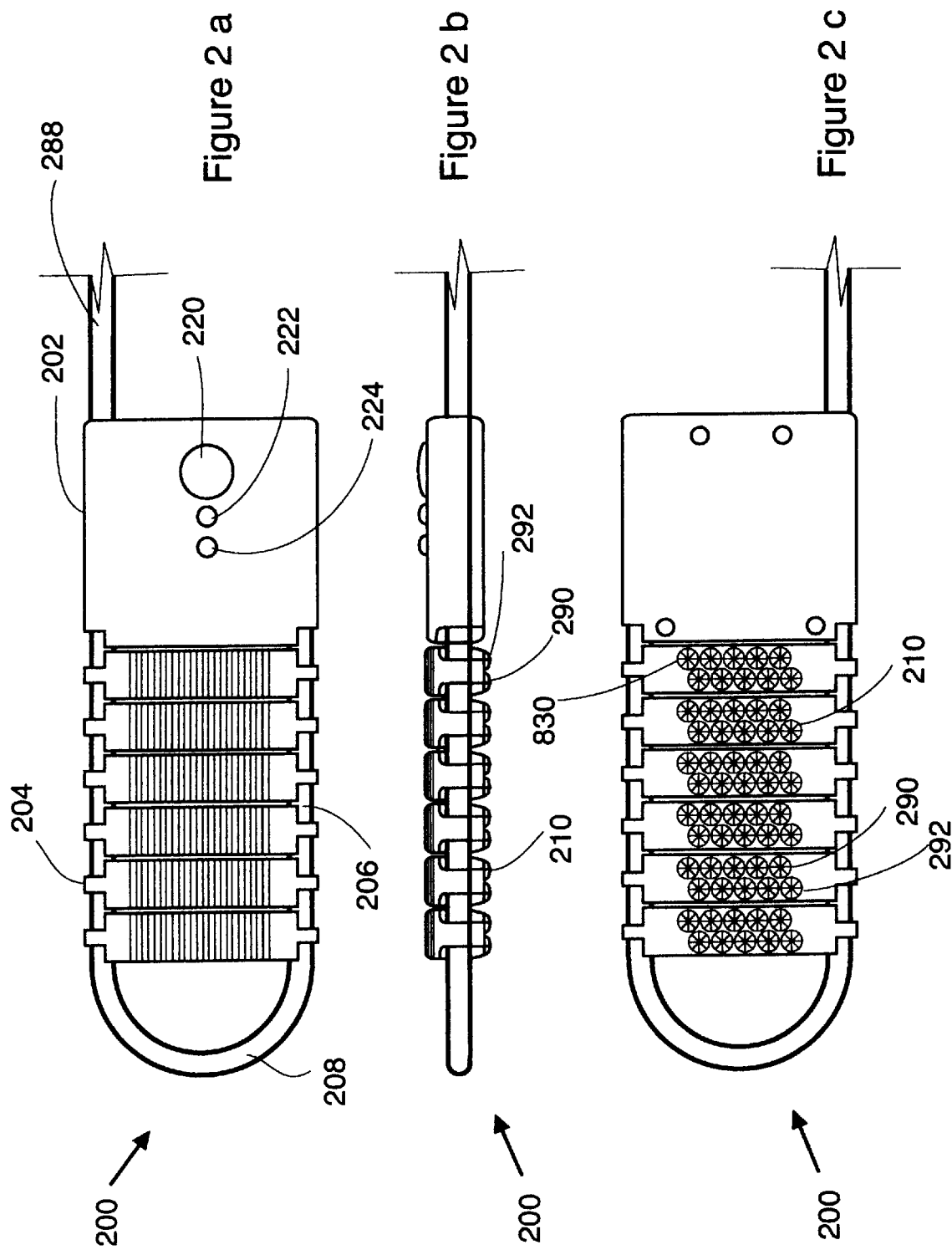
FIGS. 2(a)–(b) show a tip, side and bottom view respectively of a flexible treatment head.
Figure 3:
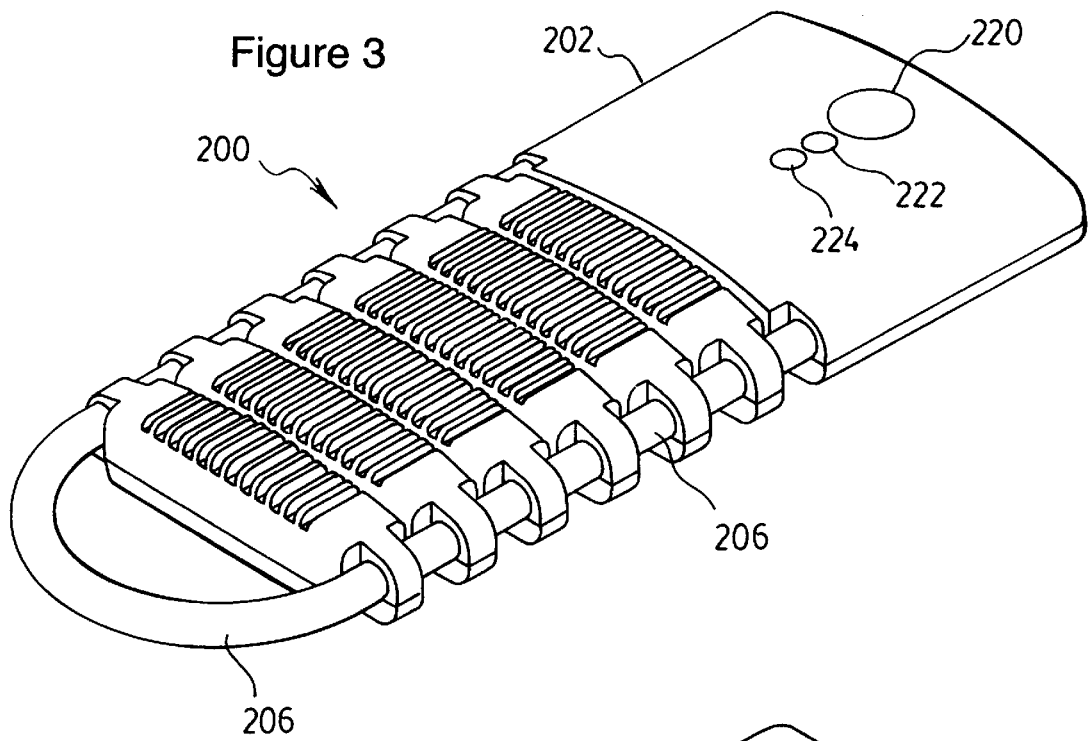
FIG. 3 shows a perspective view of the top of the flexible treatment head.

Manual control of the head 200 is provided by a switch 220 and two indicator LED's 222 and 224 which as seen in FIG 2(*a*) are mounted on top of control pod 204. The switch 220 provides the function of a start/stop button and is connected to an input port of the microprocessor 815 as indicated in FIG. 8. As a safety feature, the switch 220 must be "double-click", i.e. depressed twice in rapid succession, which sends a signal to the microprocessor 815 to enable to diode devices 210. Any single click of the switch 220 thereafter will deactivate the diode devices. The indicators 222 and 224 identify when the diodes are enabled (green) and when the head is active (red). This is a particularly important safety feature when the head is composed of infrared diode devices.

As a further safety measure, a disposable polymer-based membrane in the form of a preshaped sheath (not shown) will allow the flexible treatment head to be encased therein. This is particularly useful in open wound applications where there is risk of infection. The optical properties of the disposable polymer material is such as to allow for ready transmission of photon energy. Upon completion of a treatment, the sheath may be disposed of.

Single Point Treatment Head

Referring to FIGS. 7(a), (b), (c), (d) and (e) an embodiment of a point source treatment head is shown generally by numeral 700. In the embodiment shown, the treatment head utilizes a laser diode 702 which is capable of producing a small point of high irradiance. The head 700 includes an elongated, elliptical cross-section body 704 for gripping the head 700 and a nose 706 extending at an angle to the main axis of the body. As may be seen in FIG. 7(a), the laser diode 702 is mounted at the tip of the nose 706 and projects a beam at an angle to the axis of the 704. A bump 708 or protrusion is formed at the junction of nose 706 and body 704. The hump 708 allows a practitioner to apply, for example, thumb pressure to a point being treated while still having a firm grip of the body. The elliptical cross-section of body 704 also provides better grip of the body for the practitioner and the angle of the laser diode facilitates manipulation of the device while observing the area of treatment. The shape of the head 700 also allows the head to be held more traditionally like a pen, being squeezed between the forefinger and a thumb.

The nose 706 terminates in a tip 710 which is made as small as possible to facilitate applications such as laser acupuncture. An optical window 712 as more clearly seen in FIGS. 7(d) and 7(e) is positioned at the top of the head, behind which the laser diode is mounted. This arrangement provides protection for the laser diode behind the optical window while preventing build-up of contaminants and allowing the head to be easily cleaned, thermally and electrically isolating the diode form the patient. In the embodiment shown, heat produced by a laser diode during treatment is conducted away from the patient by a heat sink contained internally within the head (not shown). This combined with the optical windows maintains the surface fo treatment relatively cool.

As with the flexible head described earlier, safety features have been incorporated in the point source head to prevent ocular hazards, particularly with the use of laser diodes. Two indicator light-emitting diodes 714 and 715 respectively are provided on either side of the head 700. The position of the indicator diodes 714 and 715 provides a high degree of visibility from all angles. The light-emitting diodes utilized in this embodiment are of the bi-colour type and provide a green output when the head is enabled and a red output when the head is active. To provide a start control for the operation of the head, a proximity sensor device 716 is mounted on either side of the laser diode 702 and projects to the surface of the tip 710. The proximity sensor 716 includes a pair of contact electrodes 718,720 which when placed in contact with a suitable medium such as the skin provides a conduction path between the electrodes 718,720. Preferably the electrodes 718,720 are integrally molded from a conductive epoxy with the balance of the tip 710 molded from a non-conductive epoxy material. The electrodes are then covered with a think protective layer, i.e. paint to reduce the effects of moisture. The electrodes 718,720 are attached to conductors passing through the housing 703, a driver circuit which is composed of an oscillator whose frequency varies with the capacity of the electrode and then converts the output frequency to DC signal of varying voltage. The $\mu$p 915 monitors this voltage and when the head is in contact with the skin, a voltage of predetermined value is obtained which allows the head to be activated. Similarly, removal of the head from the skin terminates operation of the head. Thus, the proximity sensor also serves as a local start/stop switch, namely activating the head when the head is enabled and in contact with the skin and stopped when the head is enabled but removed from contact with the skin. An automatic delay may be incorporated within the head control circuitry to delay activation of the laser diode, in response to a signal from the proximity sensor, in order to avoid unintentional spurious luminous output. The proximity sensor provides an advantage to a practitioner since it allows a sequence of points to be illuminated for short durations without having to consciously or physically having to keep activating the laser diode. The laser diode used in the present embodiment has a power output that may range form 10's milliwatts to several hundred milliwatts which is calculated to produce an irradiance in the order of 1,000 milliwatts per square centimeter.

Figure 9:
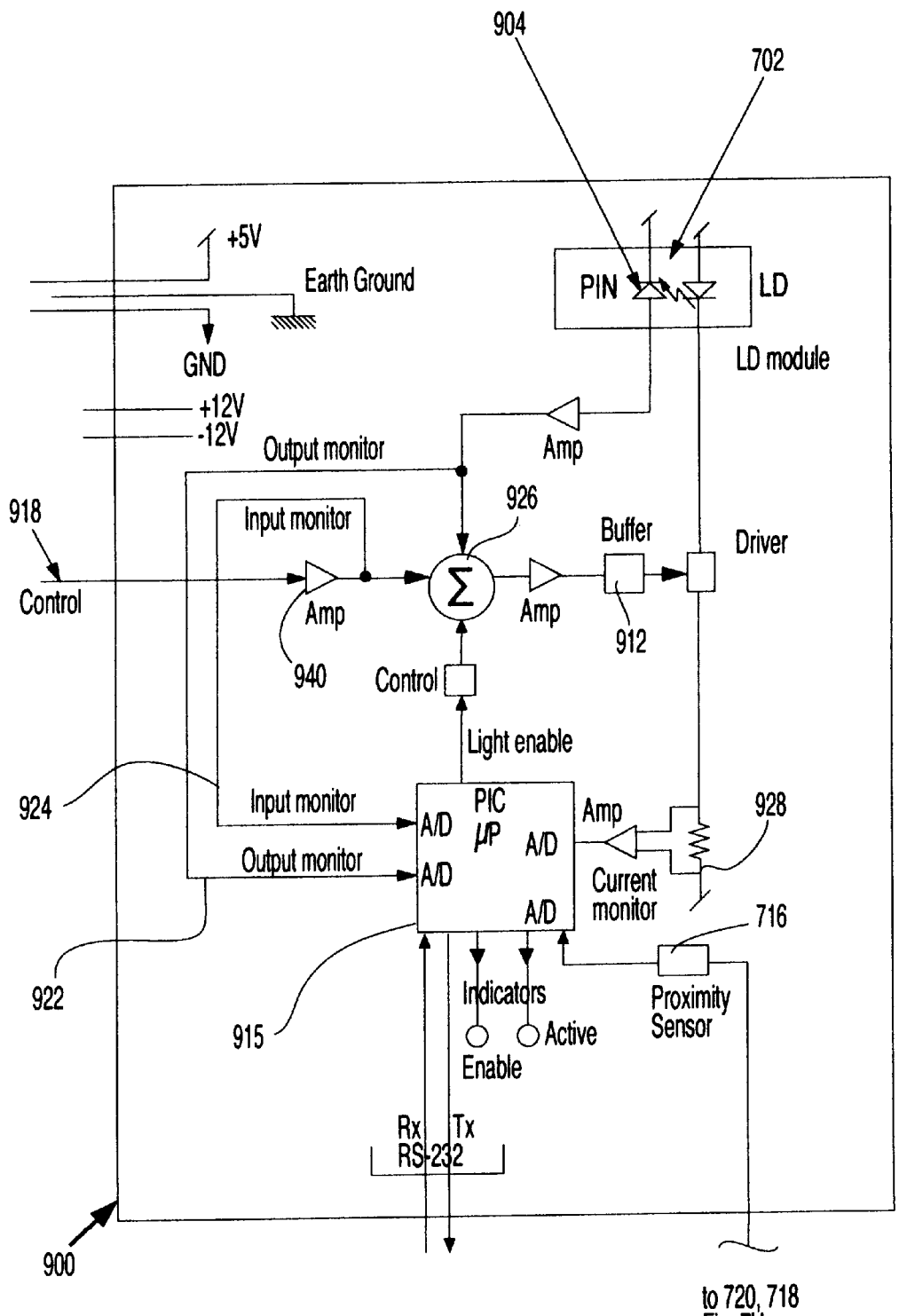
FIG. 9 is a schematic block diagram of a controlled circuit for the single diode treatment head.

In FIG. 9, an electrical circuit diagram showing the major functional blocks for control of the point source treatment head is shown generally by block 900. As may be seen, the control circuitry for the diode 702 is similar to that of the control circuitry for the flexible head as shown in FIG. 8. However, an optical feedback is provided by a PIN diode 904 which is incorporated with the module containing laser diode 702. The remaining components will not be discussed further as they are similar to that of the control circuitry described with reference to FIG. 8 but for clarity are identified by like reference numerals with 9 and the m.s.d. rather than 8.

Main Controller Unit

Figure 15:
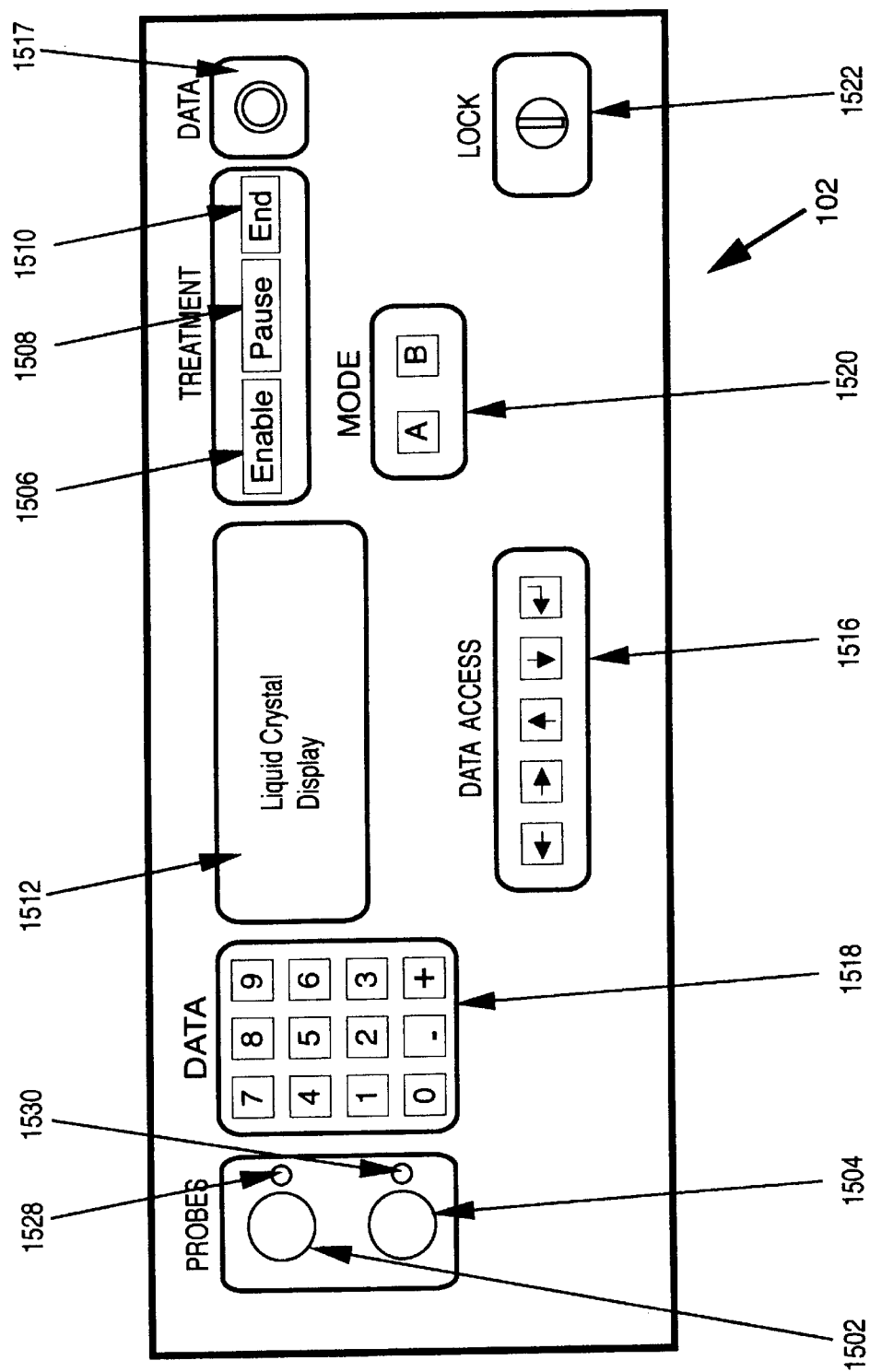
FIG. 15 is a frontal view of the main control panel.

The main controller 104 as shown in FIG. 1 is a self-contained device used exclusively to control the treatment heads and communicate with the graphical user interface. The controller 104 has two key elements, microprocessor 108 and digital signal processor 110. The controller unit 104 has a user interface 102 as illustrated in FIG. 15 or it may be controller remotely via the GUI. The main controller user interface 102 shown in FIG. 15 includes sockets 1502 and 1504, to which may be attached the treatment head control cable. A set of push buttons 1506, 1508 and 1510 provide the functions of enabling treatment, pausing treatment or ending treatment, respectively, A liquid crystal display 1512 provides display of various parameters associated with the treatment. A data entry key pad along with an associated cursor control key pad 1516 and 1518 respectively, as well as an optical incremental encoder 1517 provides means for entering date and accessing various treatment parameters. A mode selection switch 1520 provides a means of selecting various modes of operations such a preset mode and a manual mode. A key lock mechanism 1522 is provided as a safety feature to prevent unauthorized use of the system.

Figure 14:
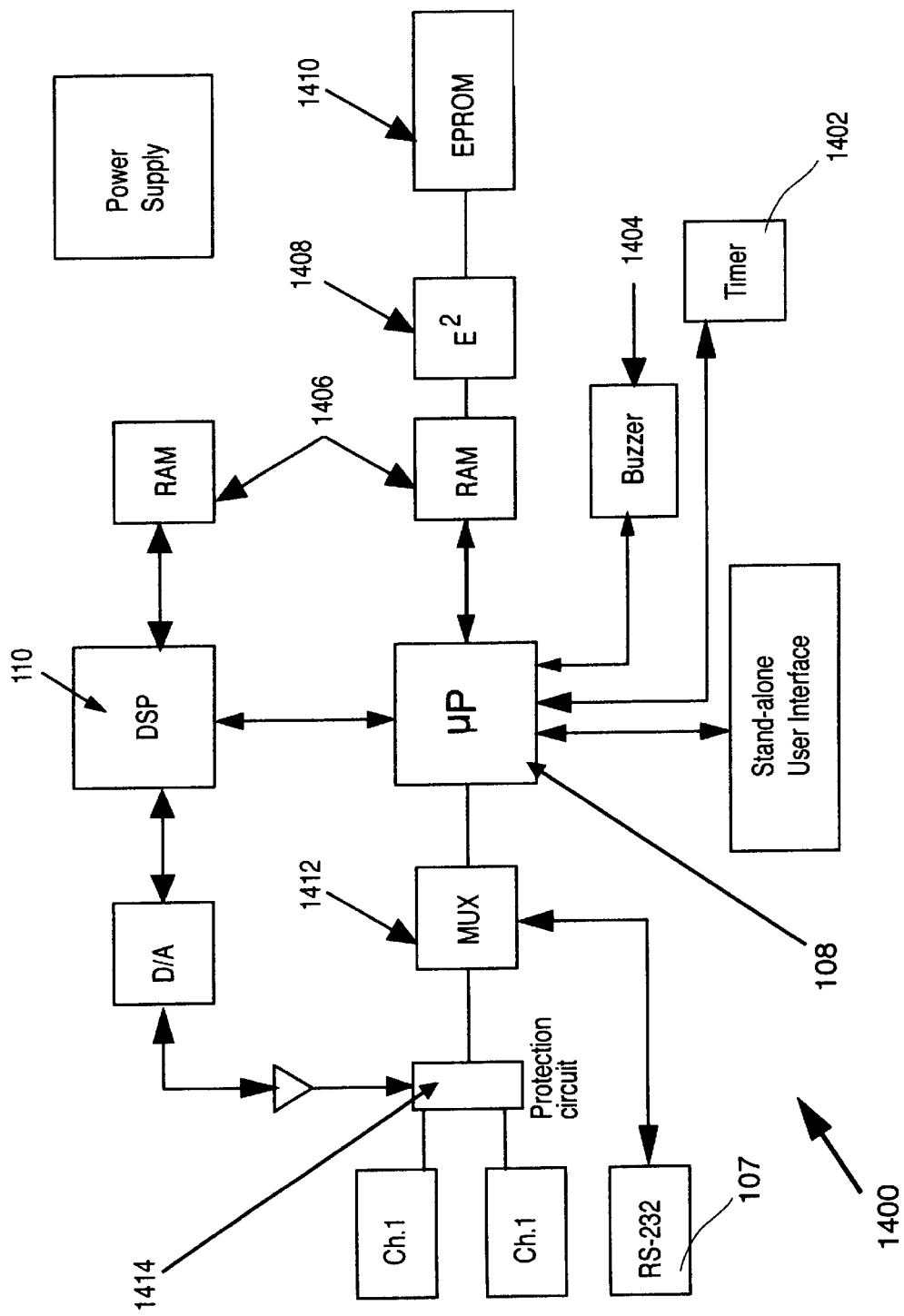
FIG. 14 is a block diagram of the main control architecture.

Referring to FIG. 14, a simplified block diagram of the main controller architecture is illustrated generally by numeral 1400. The microprocessor 108 shown in FIG. 14 acts as a central processor for handling the intercommunication functions between the DSP 110, treatment heads and the main controller user interface and RS232 interface via The GUI. A timer 1402 is settable by the microprocessor 108 to control the time of treatment and a buzzer 1404 connects to the microprocessor and provides audible indication of user significant events. The microprocessor 108 is associated with random access memory (RAM) 1406 as well as user programmable memory in the form of E²PROM (for storing preset treatment parameters) 1408 and an EPROM for storing the operating program for the microprocessor 108 and the DSP. Communications to the microprocessor 104 are switched via multiplexer 1412 between the generic treatment head ports 1502,1504 and the RS232 interface 107 to the external computer. Protection circuitry 1414 disposed between the ports 1502, 1504 and the microprocessor 108 is provided to protect the treatment heads when they are plugged into or out of the ports. The protection circuitry also serves to prevent spurious luminous output during attachment or removal of the treatment heads from the ports. Supplementary bicolor indicators are located beside each port, 1528 and 1530 as shown in FIG. 15. The indicator provides a green indication that a treatment head is attached and functional and will provide a red indication when the treatment is active.

As outlined earlier, the central microprocessor 108 is not only responsible for ensuring communication between the various components of the main controller unit but also includes programming for timing treatment, providing a specific enable sequence to the treatment heads via the ports 1502,1504, starting, pausing and stopping treatment, monitoring the ambient line sensor and controlling the treatment heads, providing head diagnostics, and controlling the treatment heads.

The DSP 110 is primarily used to synthesize various modulation schemes for the creation of treatment protocols and thus controlling the luminous output of the treatment heads. The DSP 110 allows the diodes 210 to be operated in continuous wave modulation or pulse modes. In modulation mode, the DSP 110 is further capable fo generating any repetitive wave forms such as a square wave, sine wave and triangular wave. The frequency of operation may range form 0.01 Hz to 100 kHz in modulation mode and in pulse mode, the pulse width may be as small as one microsecond.

In the pulse and modulation modes, the DSP 110 may be used to optimize the ratio of peak to average power for the diode devices. As mentioned earlier, SLDs are capable of peak intensities which may be an order of magnitude greater than their average intensities. This, however, is only possible under certain conditions. It must be noted, however, that other laser devices, such as laser diodes, generally are uncapable of producing peak pulses and will be damaged by any transients or peaks above their specified maximum average. Thus, as outlined earlier, the specific operating capabilities of each treatment head 200,700 are stored in the dedicated microprocessor 815,915 in the respective treatment head control unit, and uploaded to the central microprocessor 108 of main controller unit 104 when the treatment head is attached to the control unit. This information may include the type of head being used, either SLD or LD, the gain which may be applied to the diodes and information relating to the range of acceptable duty cycles and periods.

For most laser devices, such as LDs, the operating parameters such as duty cycle and frequency are fixed.

In the case of an SLD, when operated in modulation or pulse mode, and the period and duty cycle is small, the currents through the diode may be much larger than average. Systems, currently available using SLDs, normally operate at a fixed frequency and duty cycle and thus the operating parameters are fixed. In the preferred embodiment, the system is capable of operating over a wide range of parameters and automatically optimizes the peak to average intensity applied to the diodes 210 when as SLD head is recognized.

Figure 12:
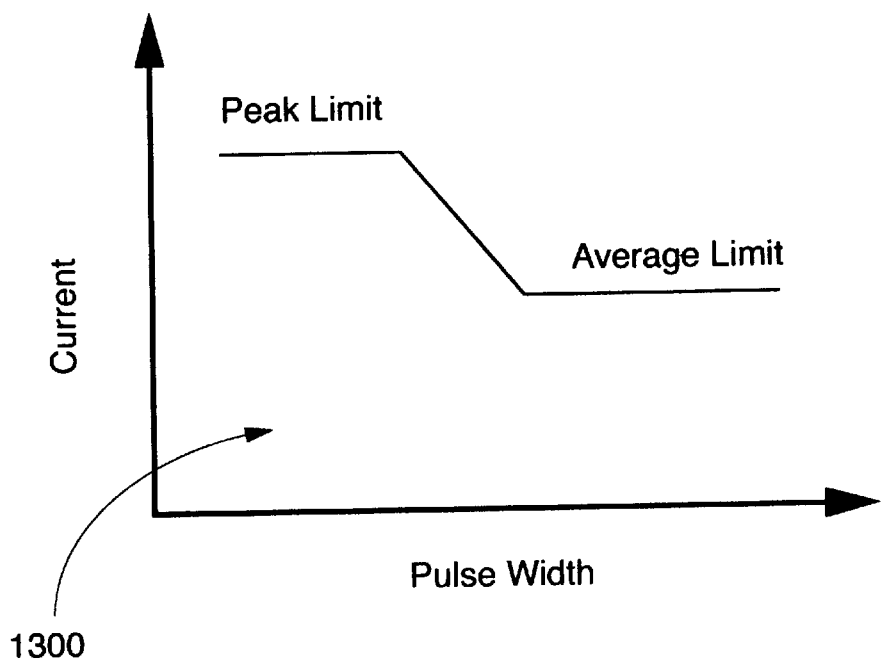
FIGS. 12 and 13 are graphs showing the peak average optimization for the diode current.
Figure 13:
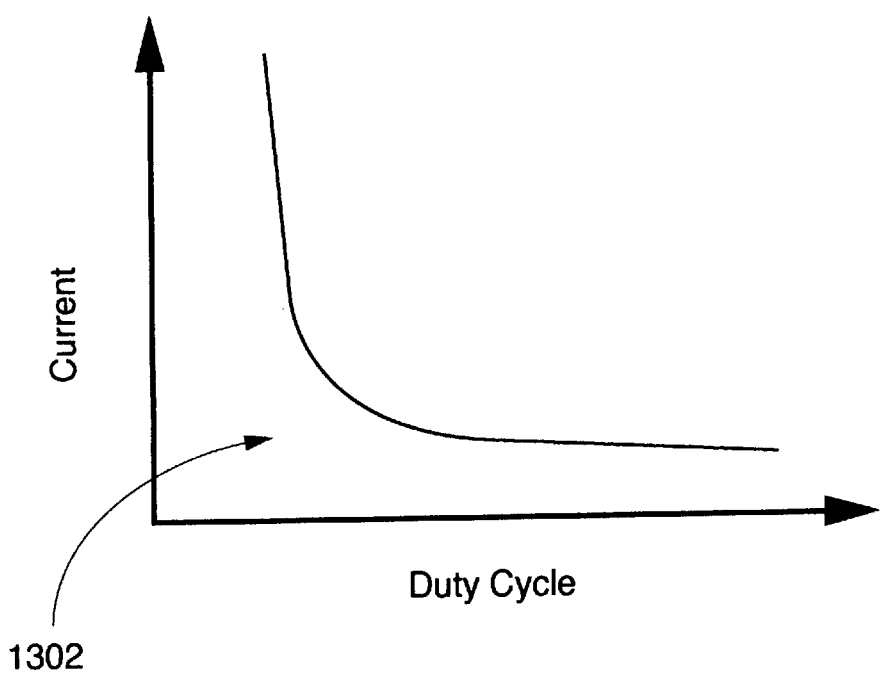
Figure 17:
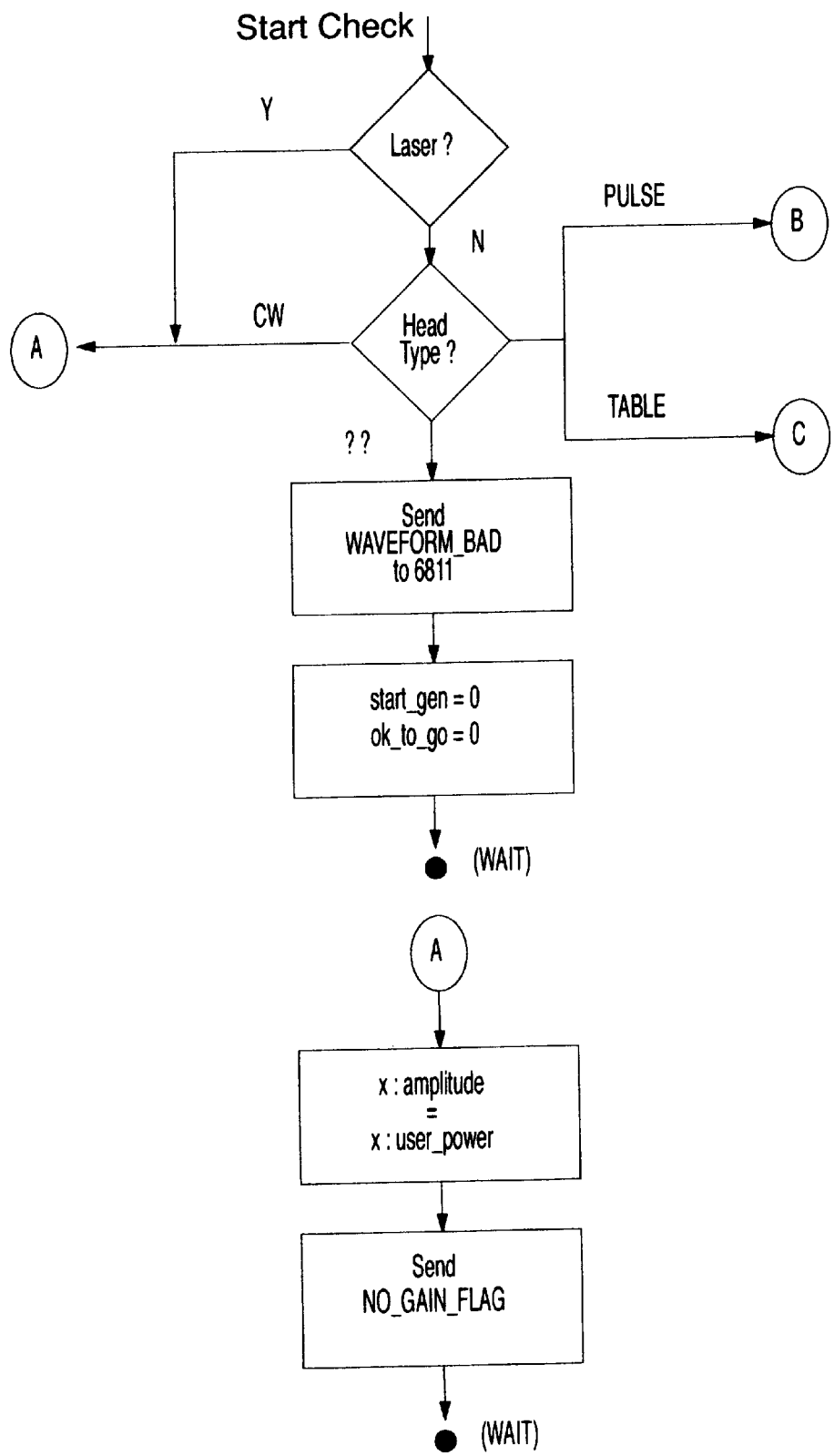
FIG. 17(a)–(c) are flowcharts showing the gain calculation for the digital signal processor.
Figure 17:
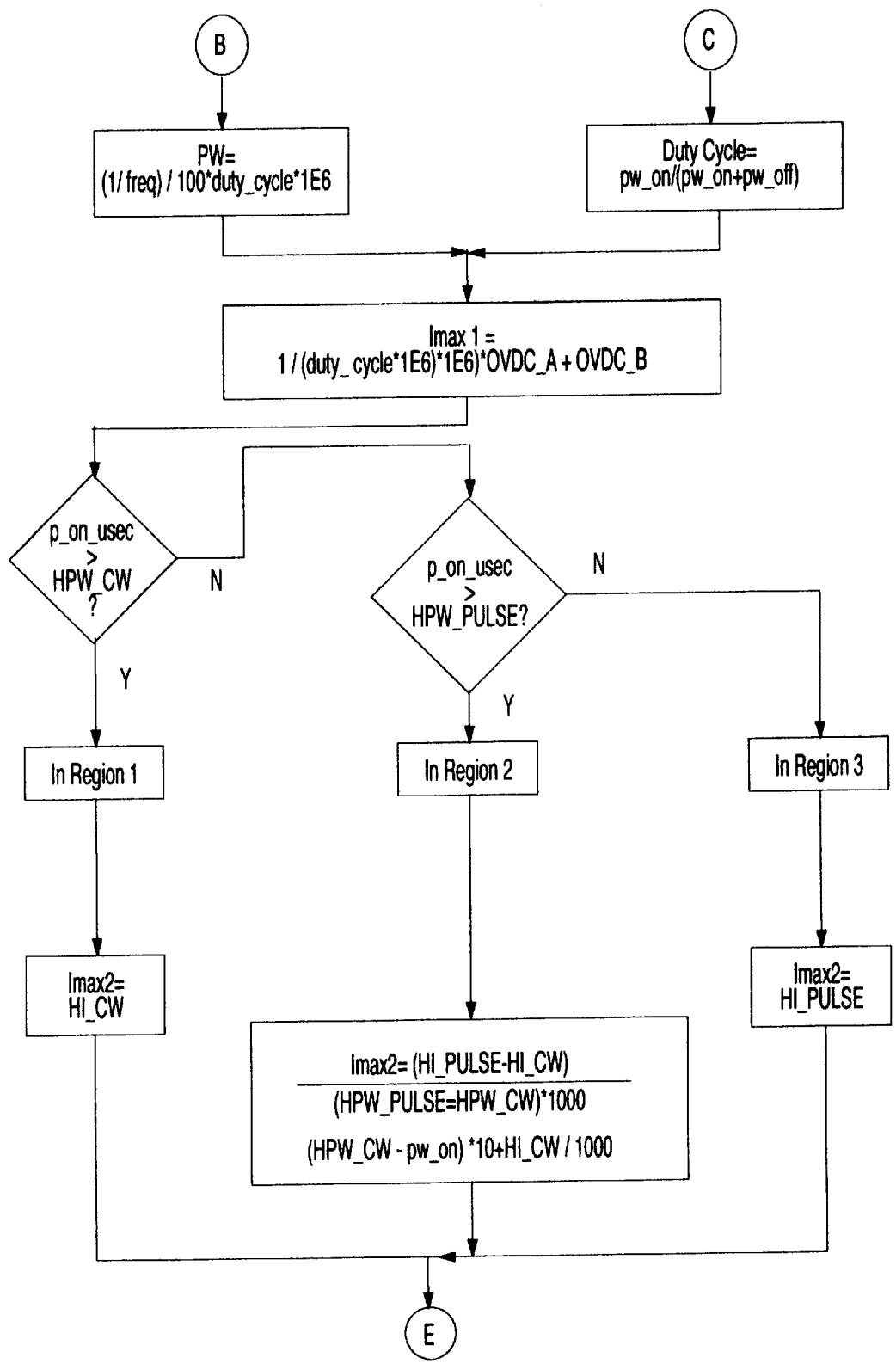
Figure 17:
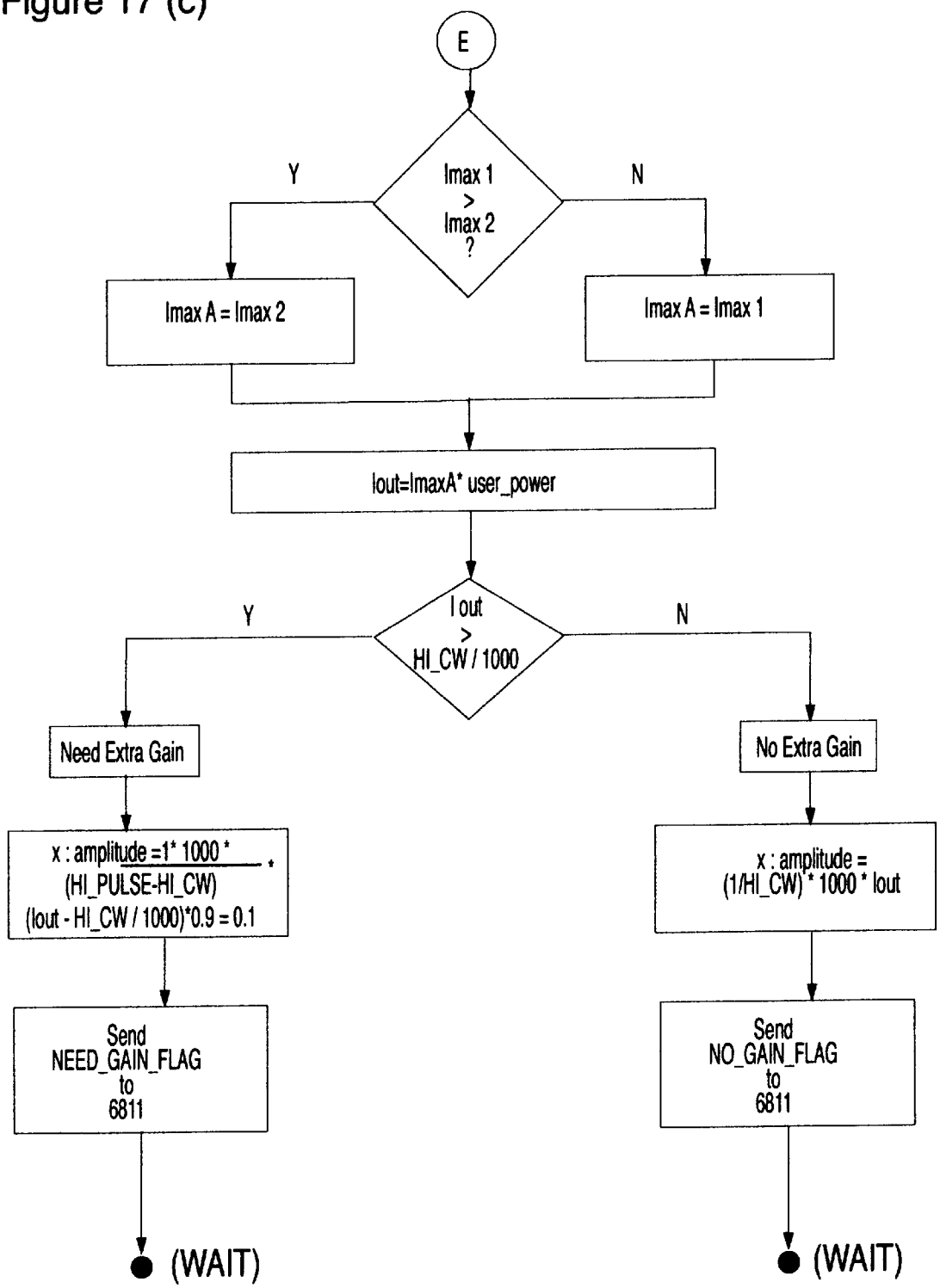
Figure 18:
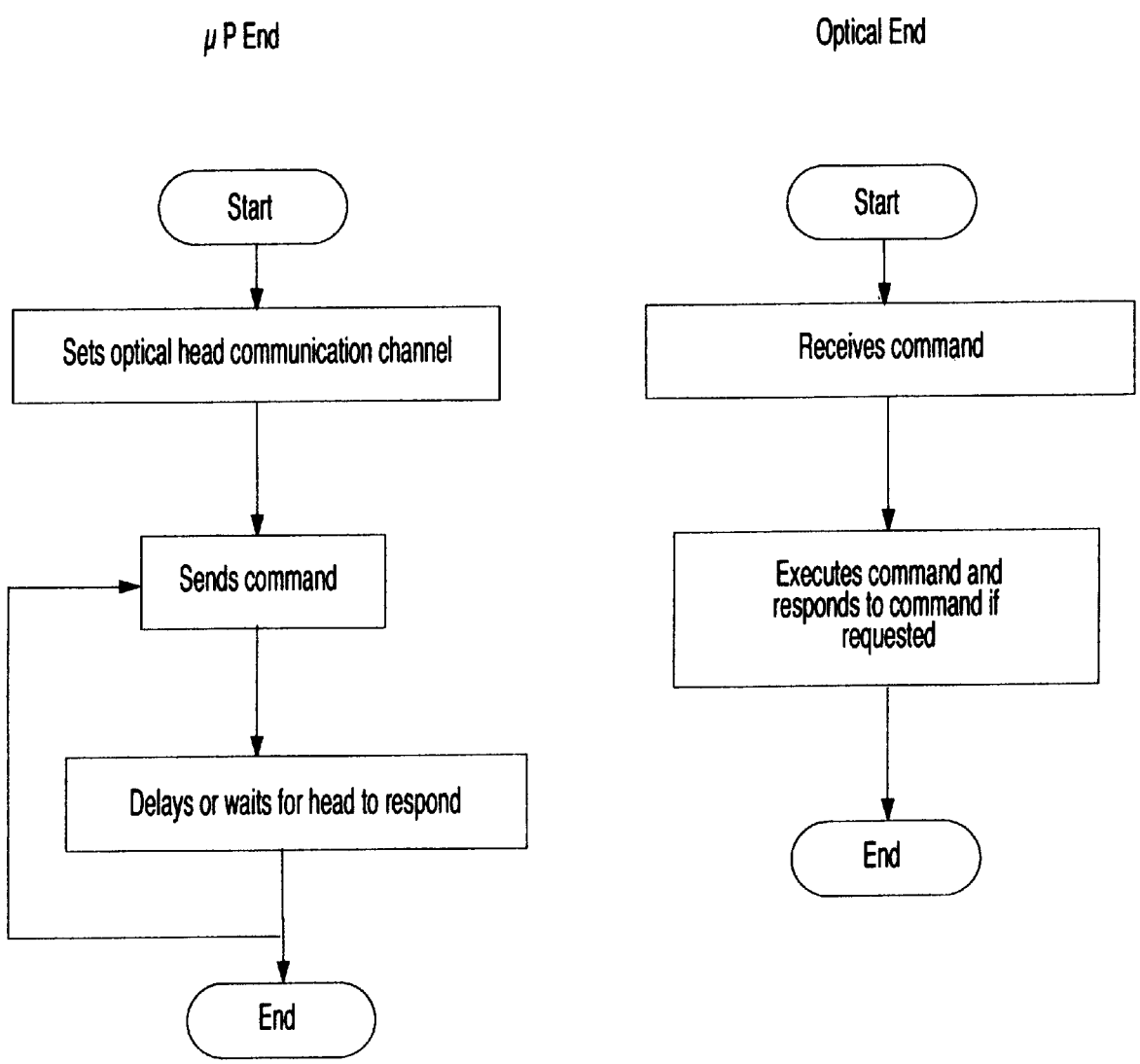
FIG. 18 is a flowchart showing the communication of messages between the microprocessor of the main control unit and the treatment heads.
Figure 19:
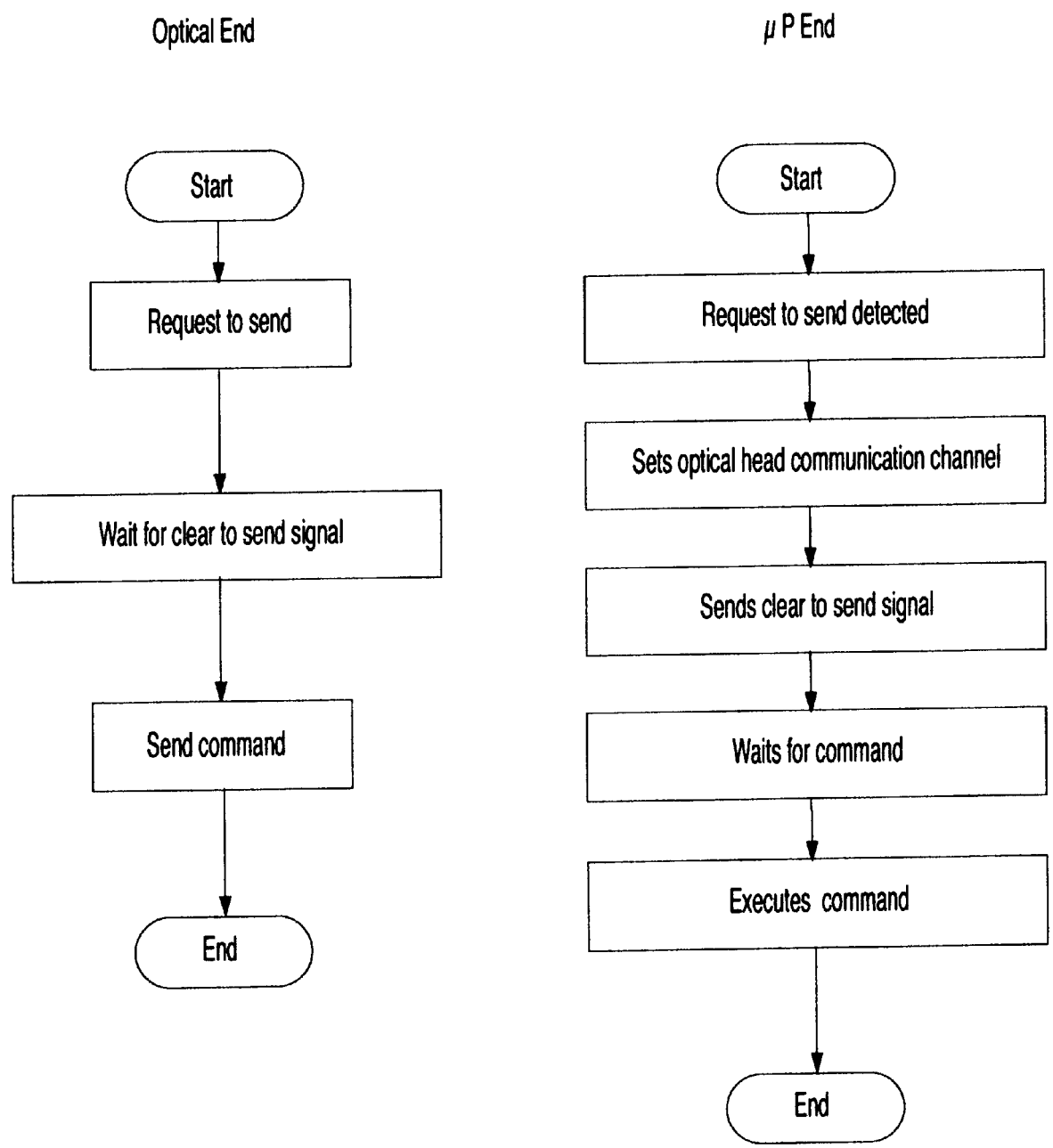
FIG. 19 is a flowchart showing the flow of messages from the treatment head to the microprocessor in the main control unit.

FIGS. 12 and 13 illustrate the operating characteristics of SLDs with a graph showing the maximum peak pulse current versus the pulse width of the SLD identified as numeral 1300 and a graph showing the maximum pulse current versus duty cycle identified as numeral 1302. The graph of 1302 indicates that the duty cycle must be low in order to achieve a high peak intensity. The maximum current may be calculated by the following equation:

$$I_{max} = \left(\frac{1}{dutycycle} \times A\right) + B$$

where A and B are provided from the manufacturer's data sheets and are specific for each device. As well, the pulse width must be small to achieve high peak intensity. The graph 1302 is divided into three sections. As shown, for high pulse widths, the maximum current allowable will equal the average while for various short pulse widths, the diode current will reach the peak limit. In the region between the two extremes is a transition region allowing varying degrees of increases in peak current. By determining which of the two values of current ie. Imax or that determined by curve 1300, optimum operation of the SLDs may be obtained. The algorithm illustrated in FIGS. 17(a)–(c) shows the sequence of steps performed by the DSP for performing the duty cycle limit calculation, checking the pulse width to determine pulse width limit and setting the peak current value to the highest possible of the two upper limits. A flag is then set to indicate whether gain is required. Should gain be required, the output is multiplied by a fixed gain amplifier 840 accordingly. The produce of the gain facto rand amplitude 818 equals the peak intensity. Based on the above information, the average intensity may be calculated.

Before a treatment can star, the practitioner must select the form of treatment and required operating parameters. This is facilitated by the GUI 106.

Graphical User Interface

Figure 21:
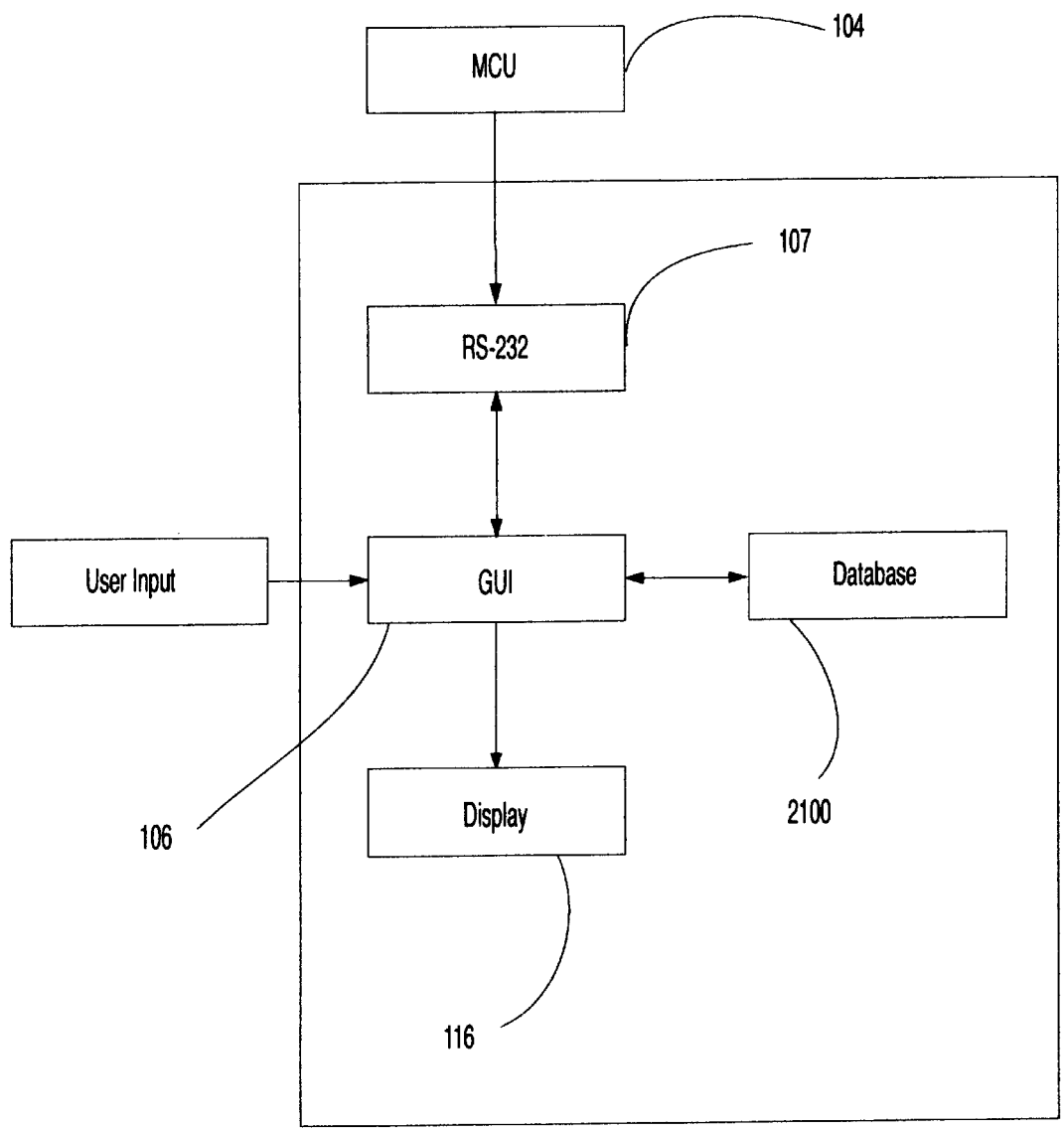
FIGS. 21(a),(b)-32 show a parameter input and control screens making up the graphical user interface.
Figure 21:
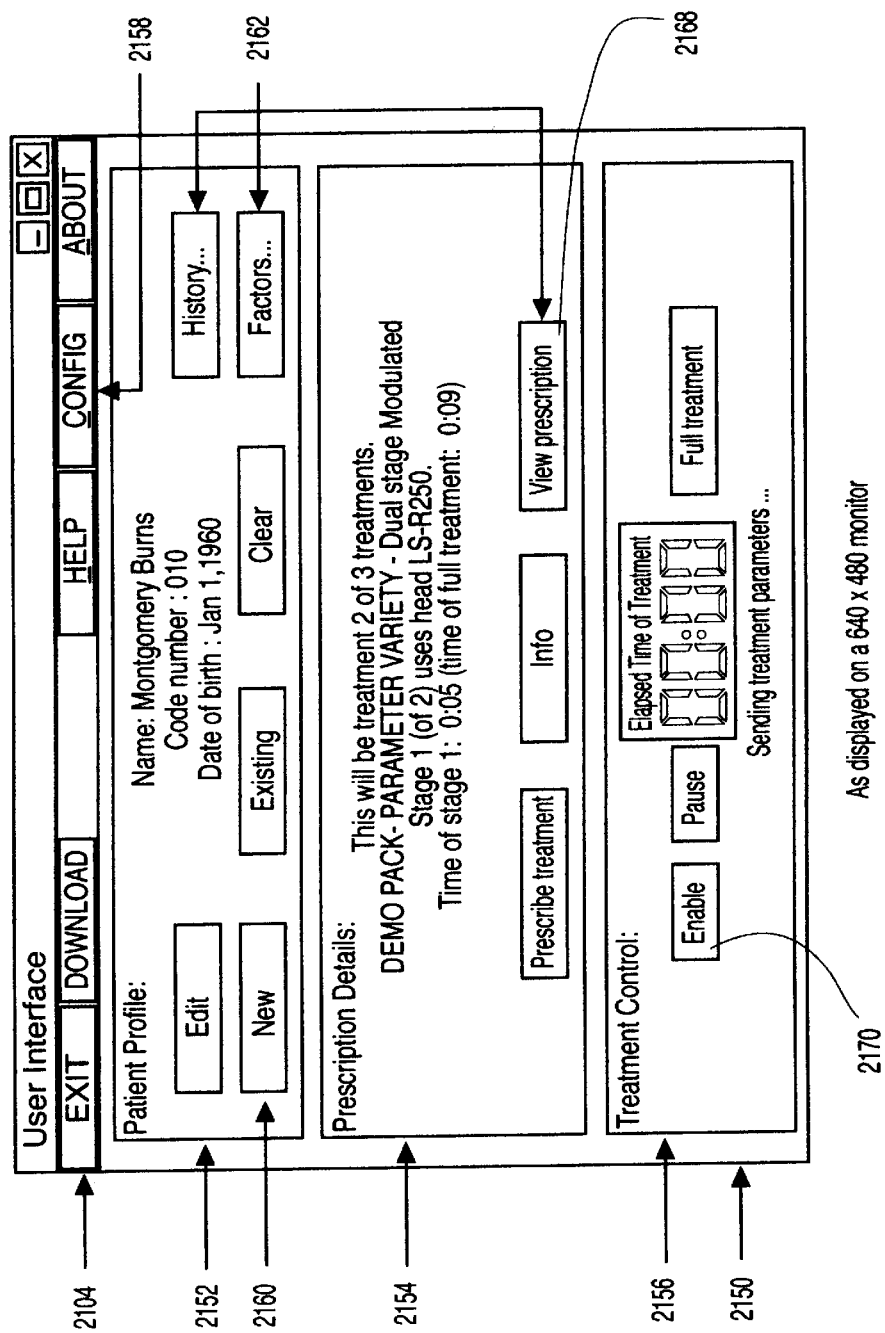

FIG. 21(a) shows the interaction between the graphical user interface program 106, the display 116 and the main controller unit 104 via RS-232 interface 107. The GUI program also interacts with a database 2100 which in the preferred embodiment resides on the computer 105, and responds to events which include user input from a keyboard 117 or a mouse 118. The GUI program 106 is composed of a number of screen displays. The preferred embodiment contains a main screen 2150 which provides access to four main groups of further screen objects, each group of screens is associated wit patient information 2152, treatments 2154, device control 2156 and program configuration 2158.

FIG. 21(b) depicts the main screen display 2150. This screen provides a menu bar 2104 which is divided into user input areas. The screen is further divided into a patient profile area 2152, a prescription detail area 2154 and a treatment control area 2156. Each of these area includes a series of command buttons 2162 for accessing the other screens associated with that group. For example, by clicking on the NEW command button 2160, a new patient screen is displayed by the GUI program in FIG. 22(a). the new patient screen includes input areas for patient name, patient code number and date of birth. An ACCEPT button allows the new patient data to be saved in a database. Referring to FIG. 22(b), an existing patient may also be selected form a scrolling list which is provided by the select patient display. A display as shown in FIG. 22(c) is accessed form a FACTORS button on the new patient screen in FIG. 22(a) or from the main screen in FIG. 21(b) and is used for setting various patient factors such as age, complexion and build, each of which has some bearing on the treatment protocols selected. In the embodiment, each of these patient factors is divided into subcategories which are assigned a scale factor. This scale factor is then used to increase or decrease the total treatment time for that patient. Thus, standard treatment protocols may be altered to account for an individual's physical characteristics. This not only makes for a more effective treatment but also reduces the amount of knowledge that a practitioner required in order to personalize treatments.

Figure 23:
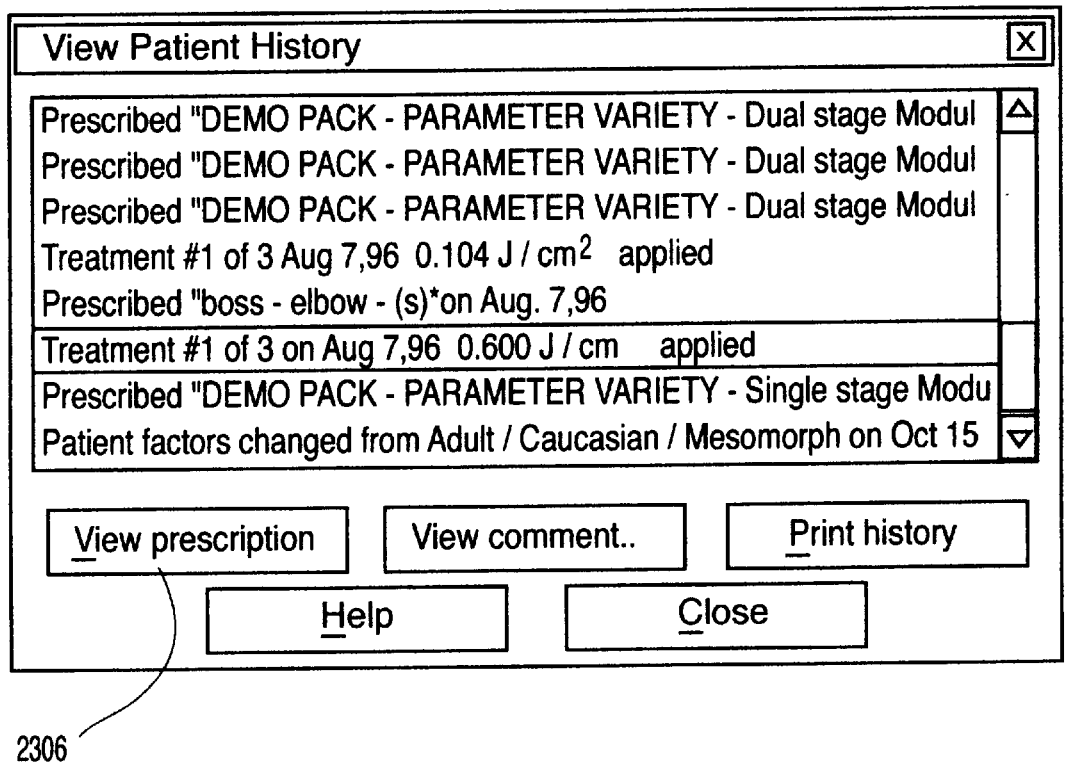
Figure 23:
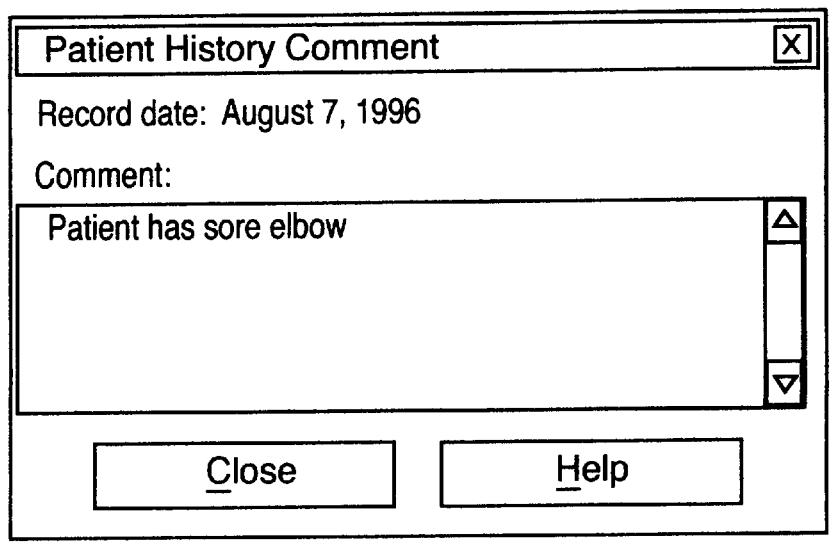

All patient related information is saved in database 2100. All treatments administered to the particular patient are then recorded in a patient history that is accessed from the main screen of FIG. 21(*b*) through the "HISTORY" button. As shown in FIG. 23(*a* ), the Patient History screen includes the treatment protocol used, dates of treatments and energy density applied and specific details of the treatment protocol. The user also has the ability to enter text-based details or comments at various stages of the treatment process such as new patient, entry, every treatment session and the end of a course of treatments. This information may be viewed via display screen as shown FIG. 23(*b*). Both the patient history display shown in FIG. 23(*b*) and the patient history display shown in FIG. 23(*b*) include view and print command buttons which allow a complete patient record to be viewed or printed to produce a hard copy.

Figure 24:
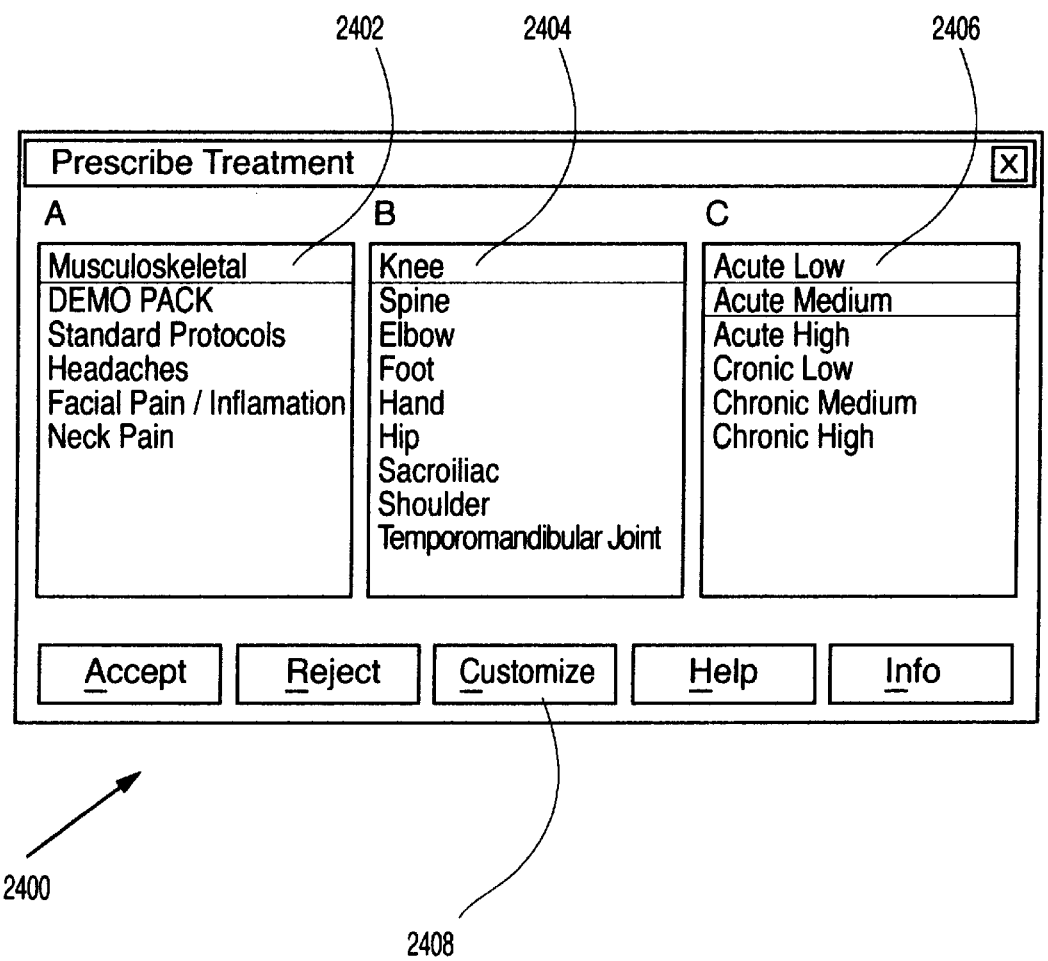

Referring to FIG. 24, a display for selecting a treatment protocol is shown generally by numeral 2400. Prescribing a treatment protocol involves the selection of a preset protocol. Preset protocols contain all the information required to implement a treatment. Protocols are stored in two groups. The first group is supplied with the system and may not be altered by the suer while the second group may be crated by the suer using a customized sub-routine. The treatment protocols are divided into three levels. The levels are labeled A, B and C as shown in FIG. 24 and indicated by numerals 2402, 2404 and 2406, respectively. For each item in column A, a corresponding list of items will appear in column B. Similarly, a selection of an item in column B will produce a listing for that item in column C. Treatment names may be based upon specific protocols or user-specified protocols, physical body regions, disease entities, various dosage levels and such-like. The details of each specific protocol may be accessed via a view prescription command button 2168 on the main screen or a custom treatment may be created via the customize button 2408. Once a treatment has been selected, it may be prescribed to the patient via the accept button 2400. All of the associated parameters are stored in the database 2100. The treatment may then be sent to the MCU and administered under treatment control via the enable button 2170 on the main screen.

Figure 26:
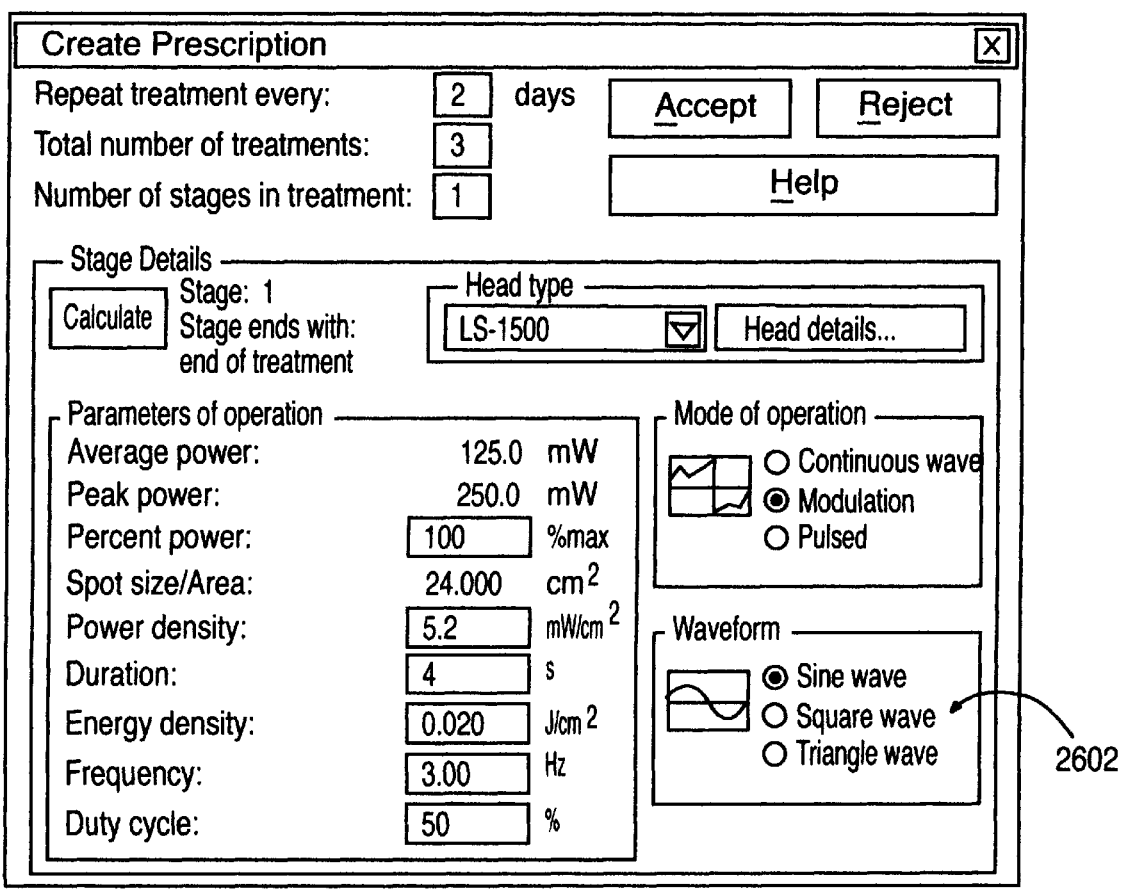

FIGS. 25(*a*), 26 and 27 display screen objects for creating prescription protocols and display corresponding head parameters for the prescriptive protocols. The screen selected is determined by which mode of operation is selected, ie. pulse as in FIG. 25(*a*), modulation as in FIG. 26 or continuous as in FIG. 27. For each prescription, the user may change how often the treatment is repeated, the total number of treatments and the number of stages in treatment. Each stage in a treatment is a set of specific operating parameters. Thus numerous stages may be set up to effectively administer multiple protocols in a single treatment. This may also include changing treatment heads as well as parameters of operation. The end of each stage may also include a forced stop allowing the practitioner to examine the patient at preset intervals. The final stage of a protocol may be repeated which is ideal for extending treatments or for treating a sequence of numerous points.

A specific head may also be selected from a listing of available heads for each stage of a treatment. The detailed specifications for each head may be viewed as for example indicated by the head parameter displays shown in FIG. 25(*b*). These parameters are specific to each head and may not be altered. This information, however, is crucial to the creation of a protocol.

Figure 28:
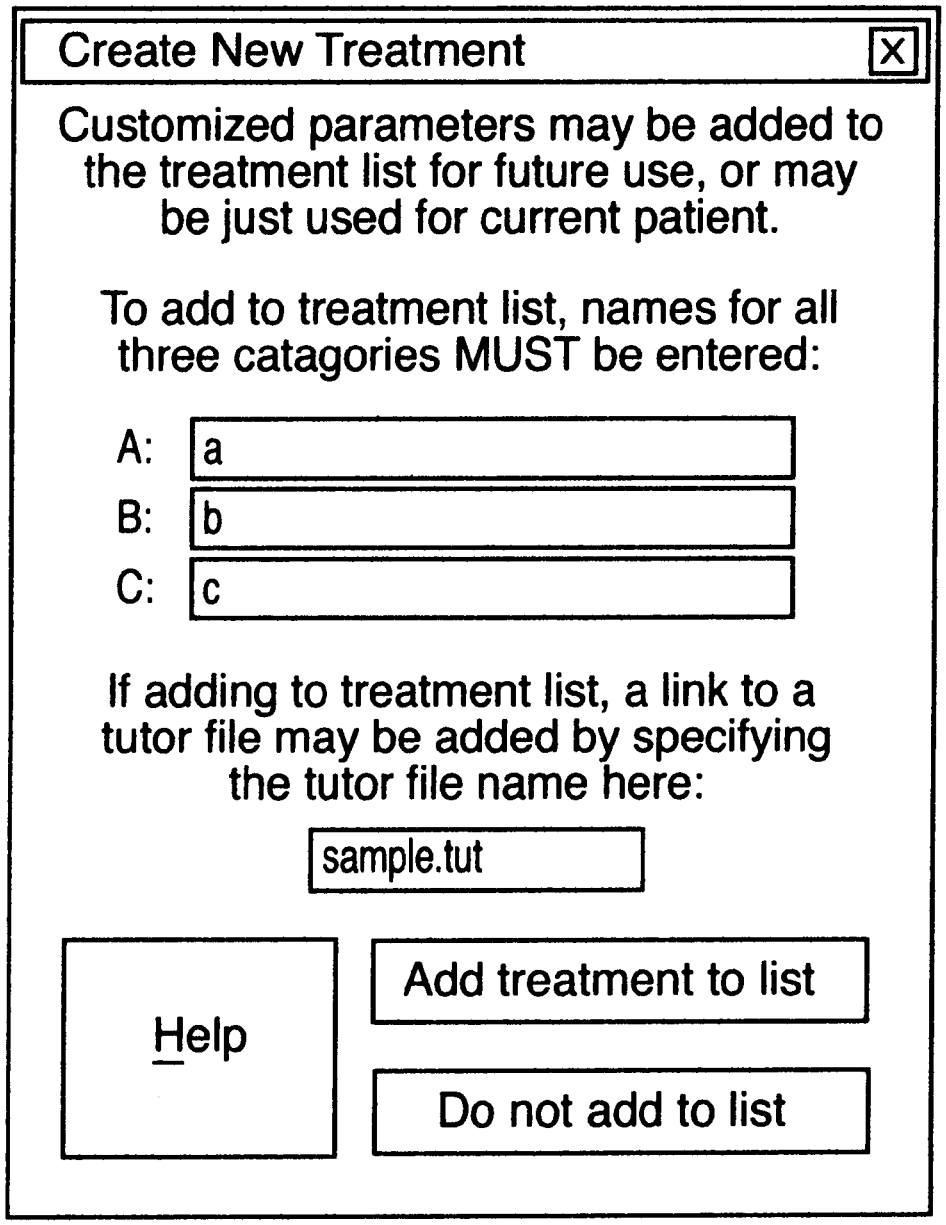

The Create Prescription display as for example shown in FIG. 25(*a*) provides under its Stage Detail section the user with a selection for the mode of operation of the particular treatment head. The mode of operation includes continuous wave, modulation or pulsed mode operation. By selecting a particular mode of operation, the parameters of displayed operation will vary accordingly. The system is also able to administer various repetitive wave forms in modulation mode including sign, square and triangular waves as indicated at 2602. A novel system feature is that the user controls luminous power via percentage rather than absolute values. The system also optimizes the ratio between peak and average power. This optimization is based upon the type of treatment head used and the characteristics of its diode, the selected frequency and duty cycle as described earlier. All other parameters such as power density, duration and energy density maybe altered. Once a treatment has been created it may be stored as a protocol as shown in FIG. 28.

Figure 20:
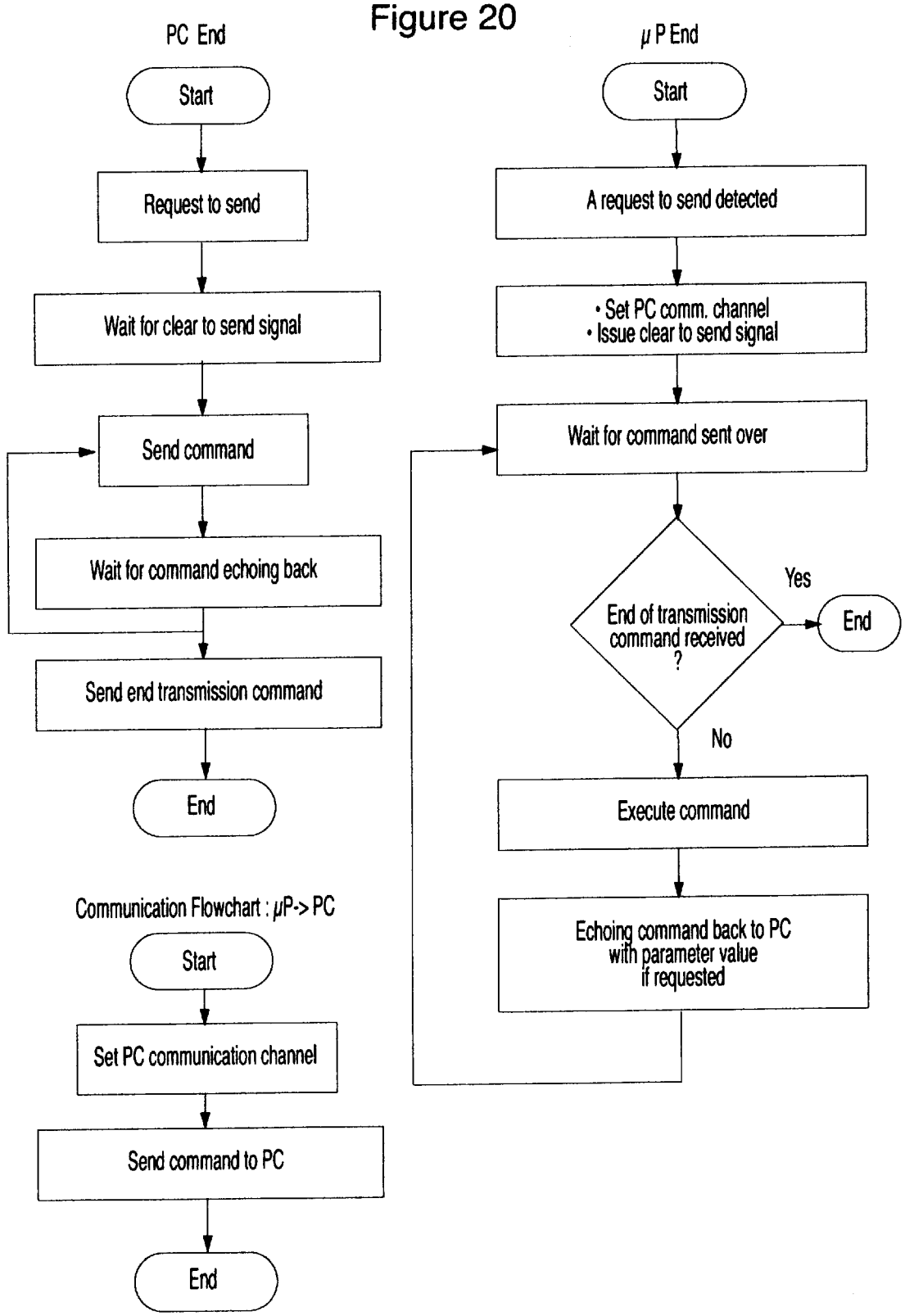
FIG. 20 is a flowchart showing the communication between the control unit and a personal computer.
Figure 29:
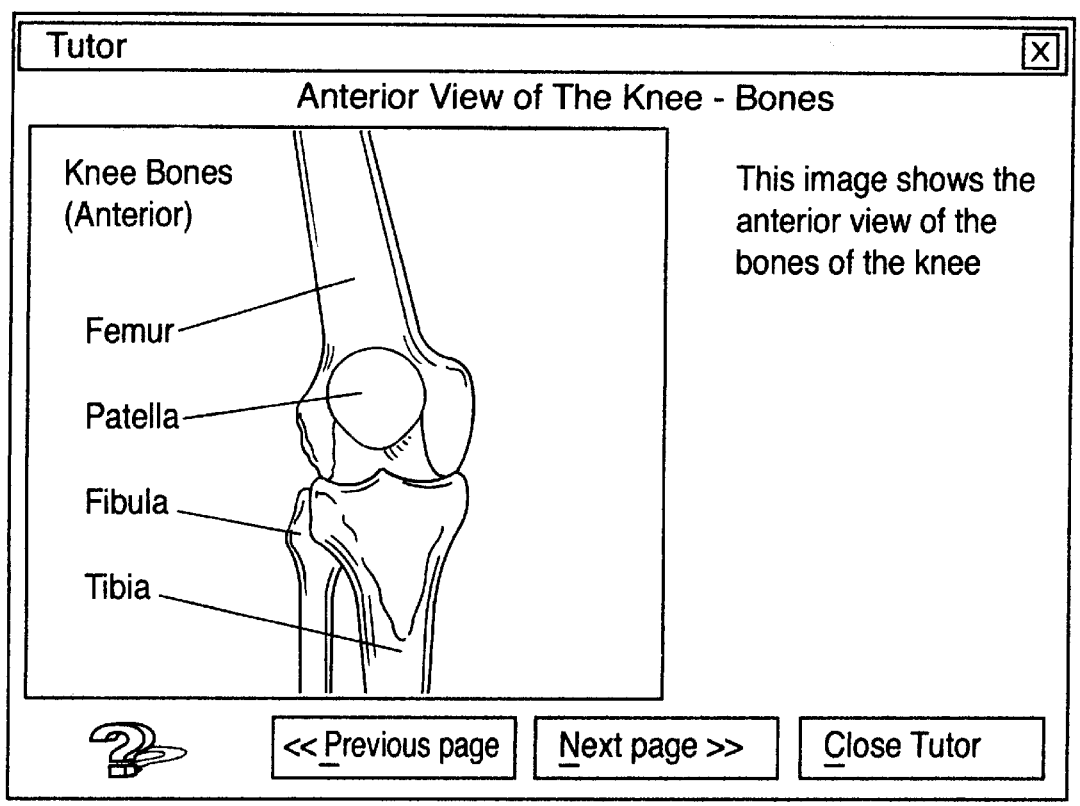
Figure 29:
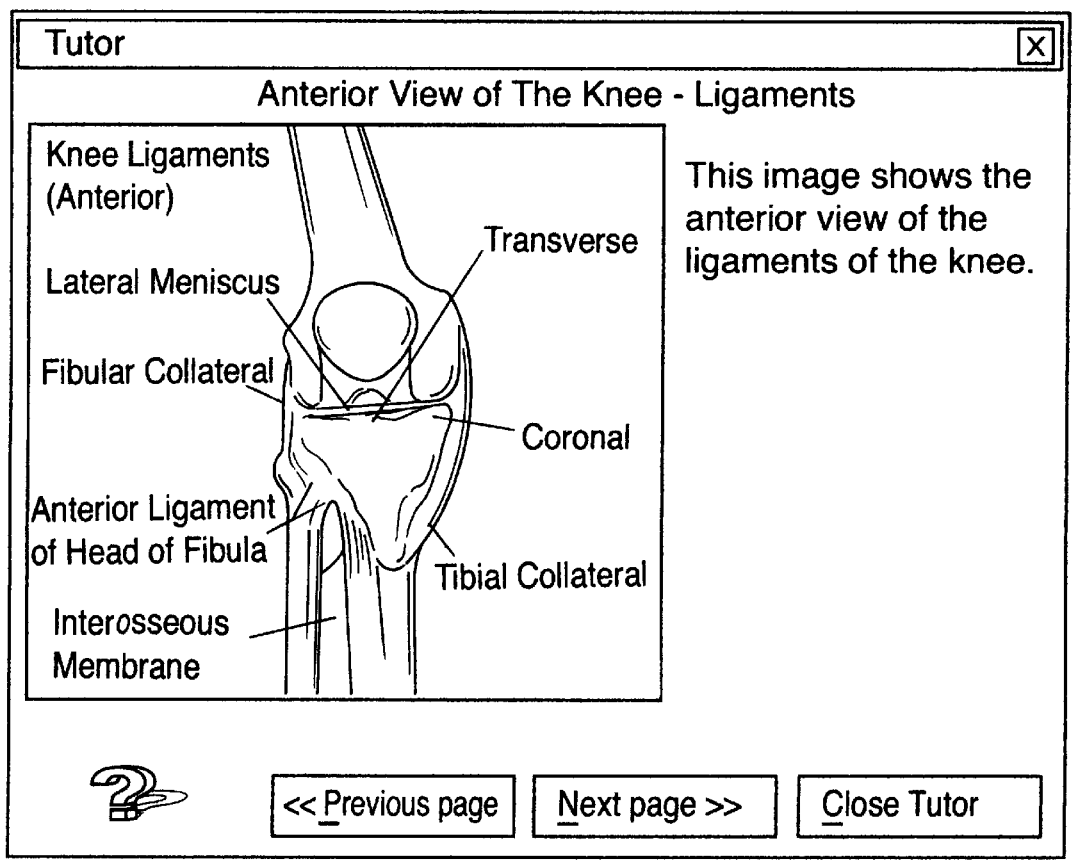

To assist the practitioner in his prescription, the GUI program also includes screen objects for an anatomical tutor. As indicted in FIG. 29, detailed diagrams of a part of the human anatomy may be viewed and linked to specific protocols. These diagrams may include specific views of anatomy, disease specific illustrations or specific information regarding treatment application and probe placement. The display may be composed of illustrations and/or text and may be layered as shown in the two illustrations of FIG. 20 to provide successive detailed views of the selected region.

Figure 30:
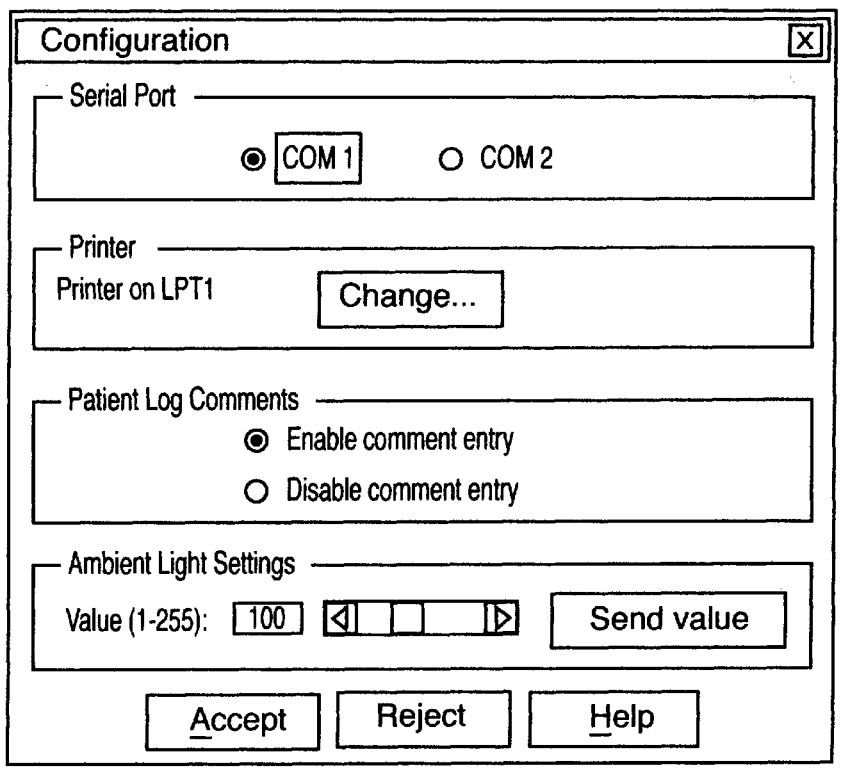
Figure 31:
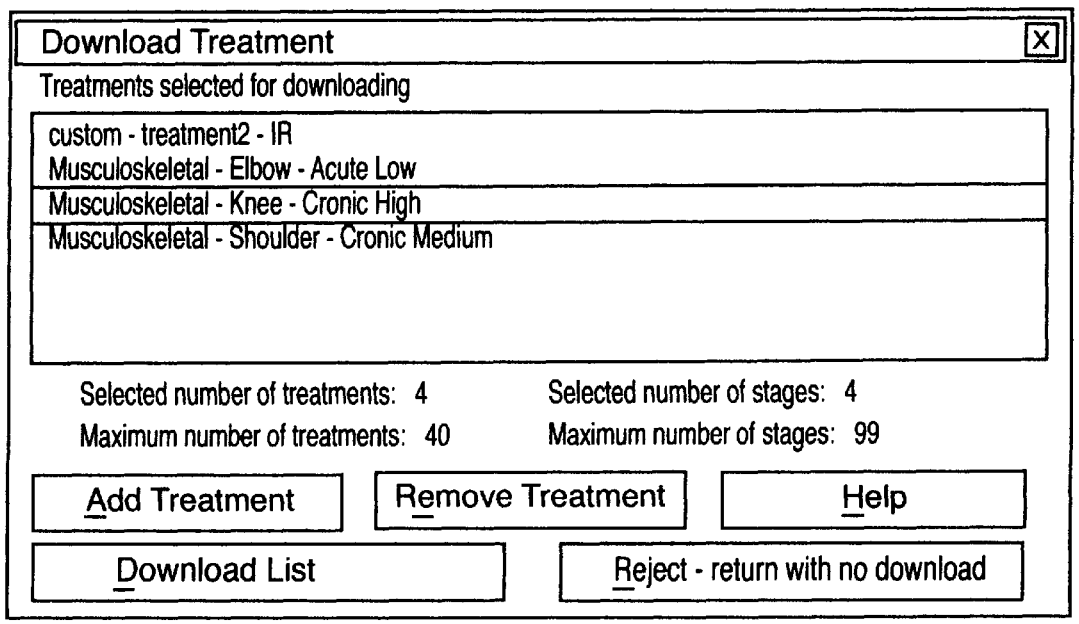

In some circumstances, it may be desirable to operate without the computer 105. In this case, the GUI 106 may be used to download prescriptions to the MCU 104. FIG. 31 indicates screen displays for initiating a download of groups of preset protocols to the main controller 104 vie the RS232 link 107, which is stored in the E²PROM 1408. System operating conditions may be set via a configuration screen as shown in FIG. 30. The download of protocols to the MCU 104 allow the access of the protocols via the user interface 102 for standalone operation.

Figure 32:
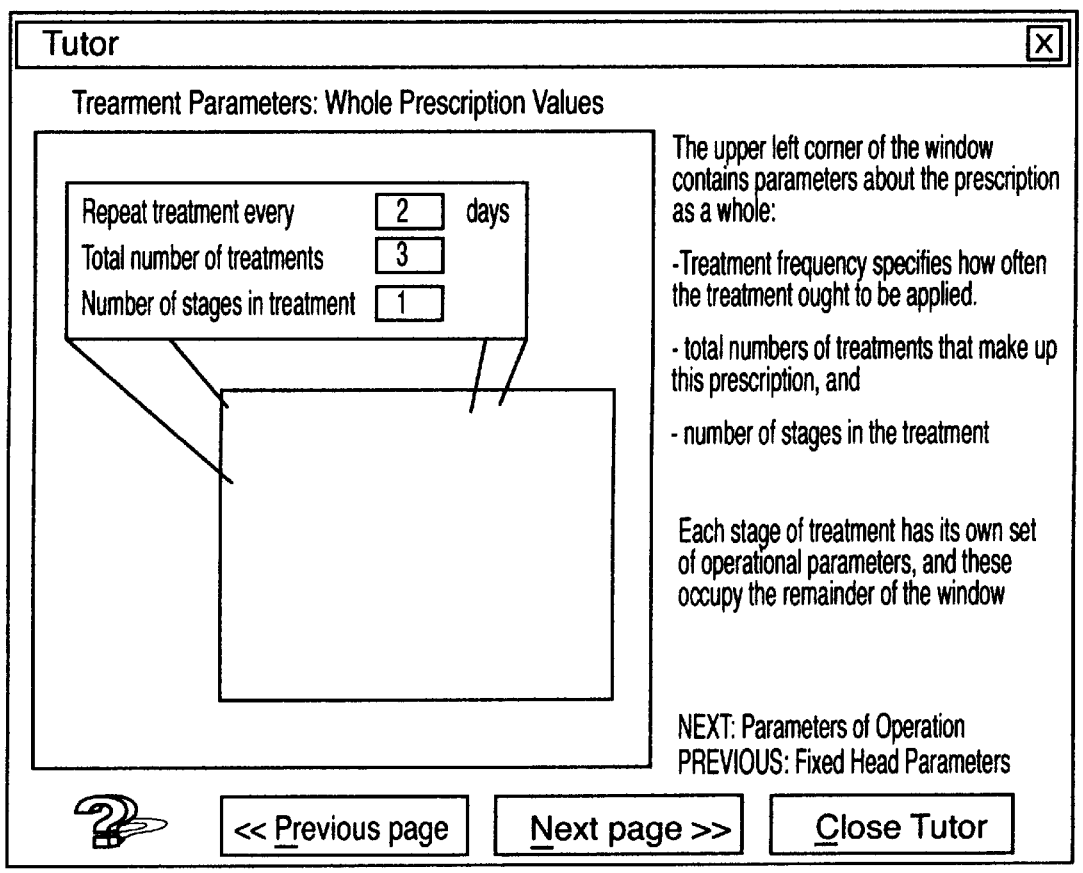

In addition, the GUI software program includes help screens for providing online assistance to a user in a conventional manner as illustrated in FIG. 32.

The communication protocol between the MCU 104 and head 2009 or computer 105 is shown schematically in FIGS. 18 and 19 and 20 and 21 respectively. The protocols are conventional in nature permitting two-way communication from the MCU 104 to head 200,700 or computer 105. In this way, treatment protocols or data may be retrieved from the computer 105 and stored in the E²PROM 1408 and information gathered from the dedicated microprocessors 815, 915 and instructions forwarded for treatment.

Having described the various components of system 100, the overall operation will be described.

Figure 16:
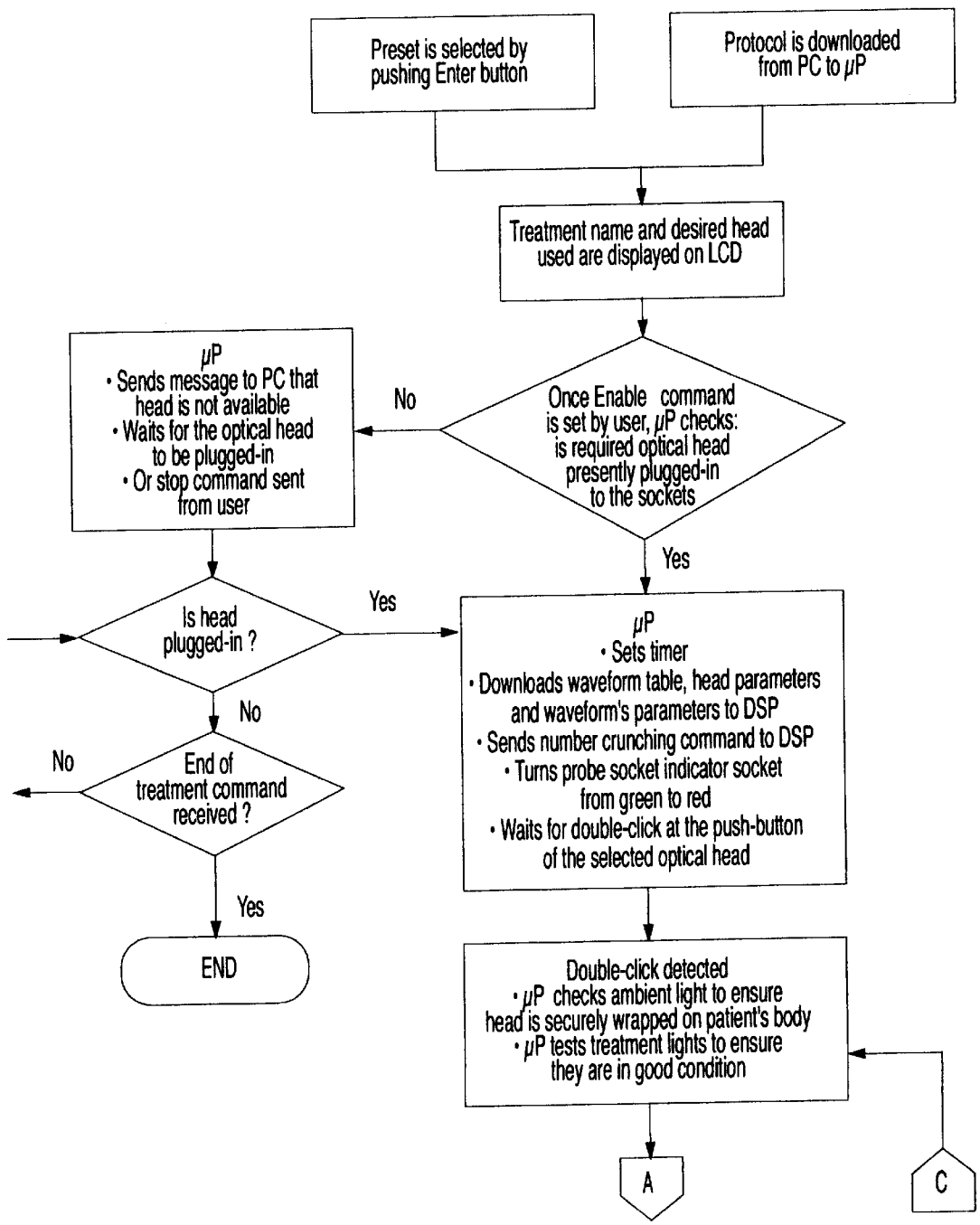
FIGS. 16 (a) and 16(b) show the overall system flow chart for the main controller.
Figure 16:
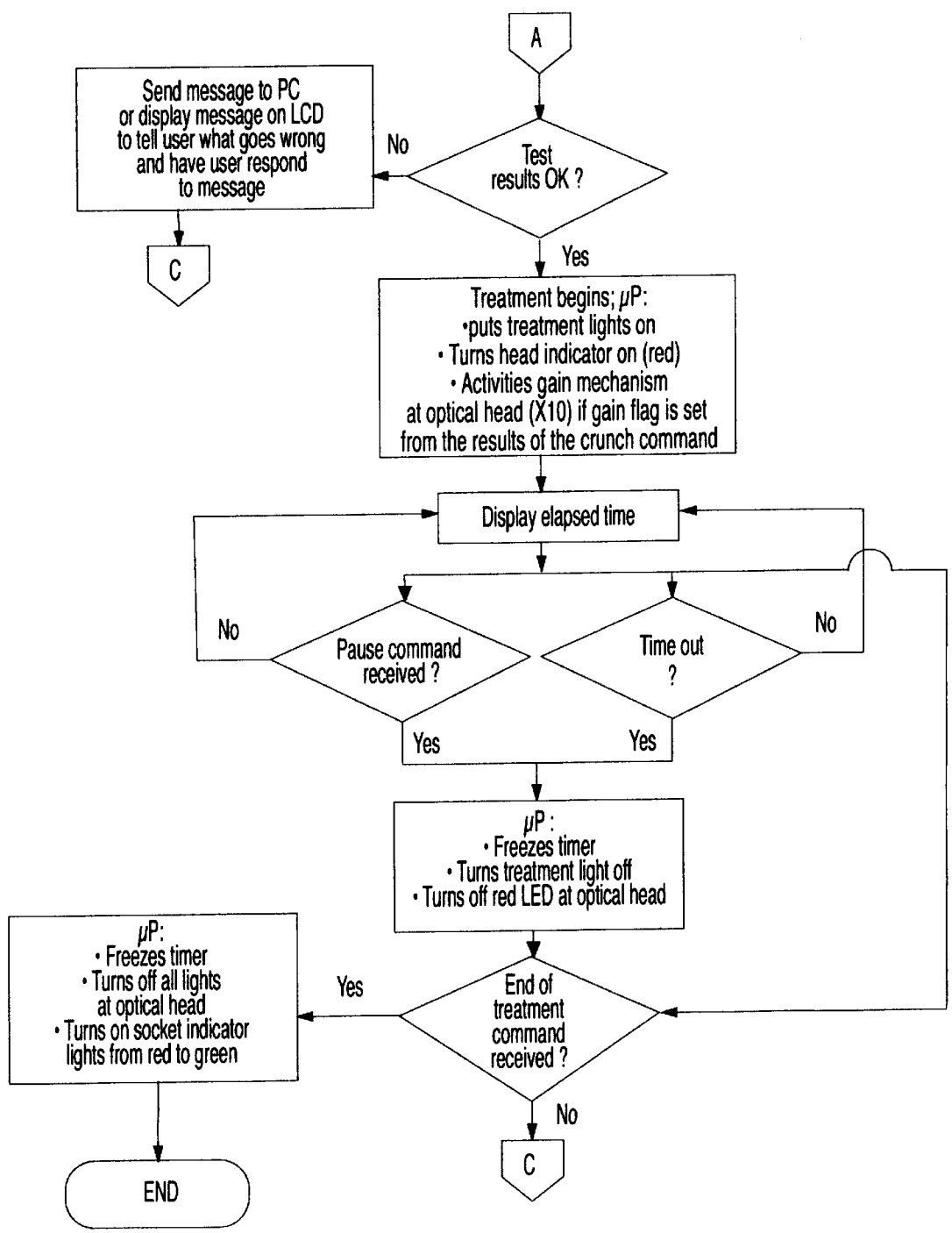

Referring now to FIGS. 16(*a*) and 16(*b*), system operation treatment may be initiated in one of two ways, either by downloading a protocol from the GUI software database to the microprocessor 108 in the main controller unit 104, or having a preset protocol stored in E²PROM 1408 selected via the data entry controls 1516 on the interface 102. In either instance, information regarding the desired treatment is displayed on the liquid crystal display 1512 and/or the GUI and all actions entered by the user directly via the control panel and/or via the GUI program. Once the treatment is selected, the microprocessor checks that the required treatment head as required by the selected protocol is currently plugged into either one of the sockets 1502 or 1504. If the required treatment head is not plugged in as may be detected for the dedicated microprocessor 108, the microprocessor 108 sends a message either to the GUI program via the RS232 link of the computer or to the liquid crystal diode 1521 informing it that the head is not available. The microprocessor then waits for the requisite head to be plugged into the socket. The program may be ended by the user. Once the correct treatment head id detected, the microprocessor sets the timer 1402, then downloads a wave form table, head parameters and wave form parameters to the DSP 110. A command is then sent by the microprocessor to the DSP to begin processing the protocol. The indicator lights 1528,1530 adjacent the socket 1502,1504 on the main controller panel is switched form green to red and the head indicator 222 is switched to green, indicating that the head is enabled, i.e. ready to perform a treatment protocol. At this time, the microprocessor 108 waits for a double click of the push-button 220 on the treatment head. Once a double click is detected, the microprocessor 108 checks for ambient light to ensure that the head is securely fastened onto the patient's body (as in the case of a flexible treatment head), or in the case of the head 700, this is automatically performed by the proximity sensor. The microprocessor 108 then tests the treatment head to ensure that it is in good order.

As seen in FIG. 16(b), should an error signal be detected at this stage, a message is sent to the PC or the liquid crystal display to inform the user of the particular error. The processor then returns to Point C on FIG. 16A. If no error message is received at this stage, the treatment begins. The microprocessor 108 turns the treatment diodes on via control signal 818 derived from the DSP 110, the head indicator light 224 on (red) to indicate the head is active, and activates the gain mechanism of the treatment head if the gain flag has been set. The main control circuit in the head 200,700 then monitors operation as described above with reference to FIGS. 8 and 9 respectively. The LCD display and or the GUI program is constantly updated with the elapsed time of treatment. At this time, if a PAUSE command is received is received or the treatment time has elapsed, the microprocessor freezes the timer, turns the treatment diodes off, and turns off the indicator LED of the optical head. If at this stage an END-OF-TREATMENT command has not been received, the microprocessor returns to point C on FIG. 16A. If and end-of-treatment command is received, the microprocessor freezes the timer, turns off all the indicators at the treatment head, and turns the socket indicator light from red to green. the sequence of operation is then completed. Further use of the head requires enablement of the treatment protocol and subsequent activation of the head.

It may be seen then that once the treatment protocol as been determined and the treatment enabled, further adjustment or control of the optical characteristics of the treatment heads need not be manually adjusted since the microprocessor within the treatment heads with its associated feedback loop ensures that the characteristics of the optical devices such as the SLDs and LDs remain accurately calibrated.

The embodiment described above provides full flexibility of treatment for a number of patients as may be required by a medical practitioner. The principles of operation may also be utilized in an environment suitable for personal use, for remote use by a practitioner, as an outpatient treatment for treatment at a clinic where a number of units may be programmed and used simultaneously. The unit may be programmed with generic protocols by the manufacturer for personal use or with specific protocols 2400 by the practitioner for prescription use.

A unit intended as a personal unit is shown in FIGS. 33–39 in which like reference numerals will denote like components with a suffix "a" added for clarity. The system 100a is self-contained having functions of the main operating unit 104a integrated into treatment head 200a. The unit is programmed via programmer module 270 from the GUI program 106 and RS 232 interface 107 through communication port 272.

The head 200a includes diodes 210a mounted directly on a flexible printed circuit board 250. The printed circuit board 250 is sandwiched between two layers of silicon 252,254. The lower layer 252 through which the diodes 210a project is thermally insulative electrically non-conductive to inhibit heat transfer to the skin of the patient. The upper layer 254 is thermally conductive electrically non-conductive and has cooling fins 1008a integrally formed in it. This arrangement has the same heat transfer attributes as described previously.

Figure 37:
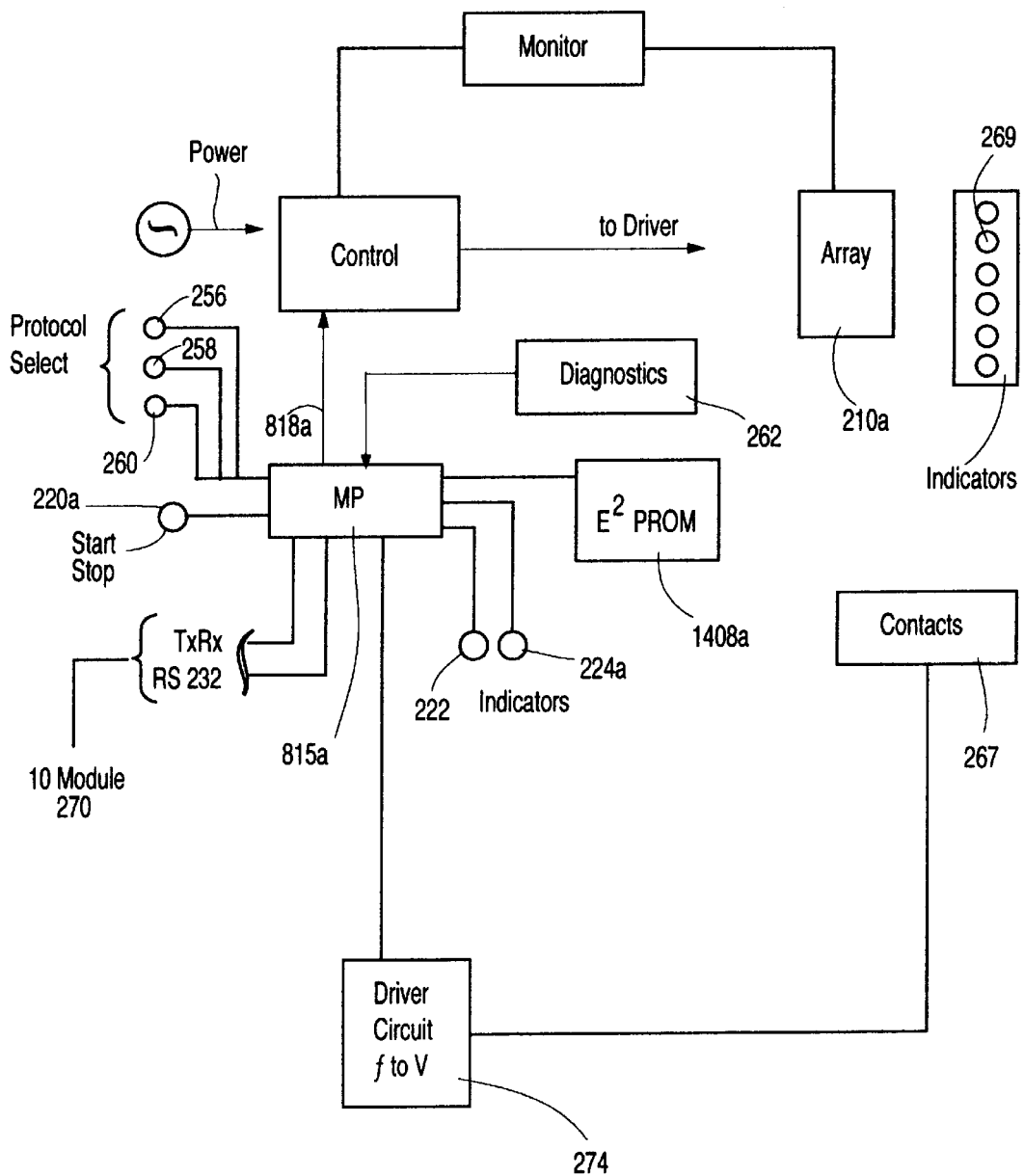
FIG. 37 is a schematic circuit diagram of the control circuit incorporated into the head of FIG. 33.
Figure 39:
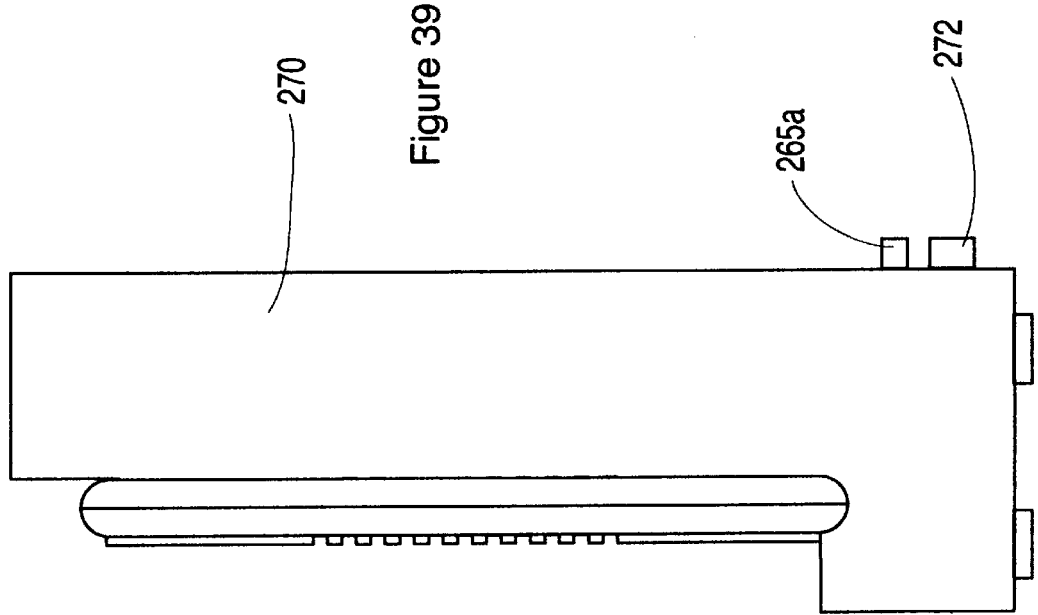
FIG. 39 is a side view of the head of FIG. 38.
Figure 38:
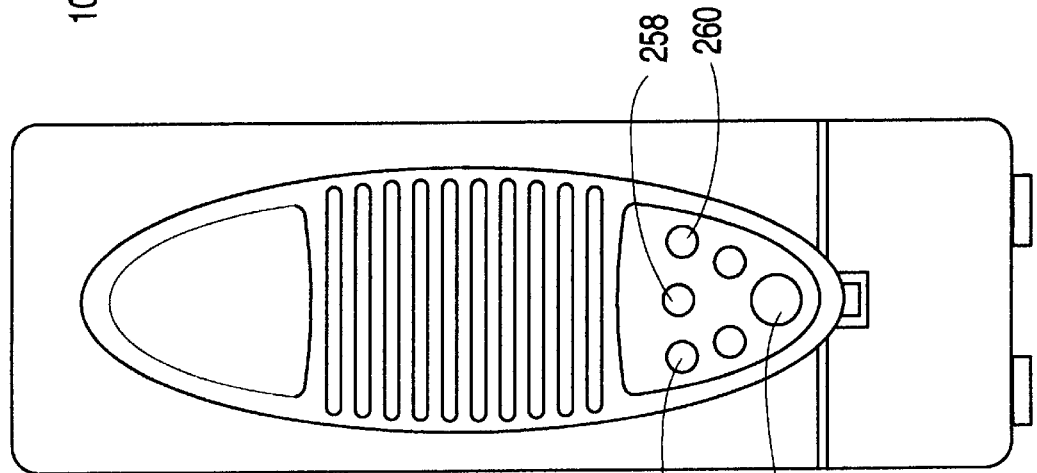
FIG. 38 is a front elevation of a still further embodiment of treatment head and associated communication interface.

The PCB 250 extends into control pod 202a and carries the electrical components associated with the main control circuit illustrated schematically in FIG. 37. Microprocessor 815a has an $E^2PROM$ 1408a associated with it in which is stored a number of different protocols received from programmer module 270. The microprocessor 815a may access a selected one of the protocols and output control signals to control line 818a to operate the SLDs 210a. A diagnostics function 262 is associated with the microprocessor 815a to monitor operation of the head 200a and communicate to the module 270 periodically.

Selection of a respective one of the protocols is provided by buttons, 256,258,260 located on the upper layer 254. Each of the buttons carries an indicia indicative of its treatment protocol, such as it s treatment level, ie. low, medium, high, or the region to be treated, ie. elbow, knee, neck, the type of ailment to be treated, ie. sprain, arthritis, tennis elbow, or a generic treatment A,B,C. Selection of one of the buttons conditions the microprocessor 815a to access the corresponding protocol.

Activation of the microprocessor 815a is controlled by switch 220a in the upper layer 254 and indicator lights 222a, 224a provide status indications to the user. A series of indicator EDs 269 surrounding the array 210a provide a visual indication of an active probe.

A strap 600a is secured to the lower layer 242 adjacent the initial array 210a and its opposite end is secured to a releasable hook and loop fastener pad 264, available under the trademark "Velcor", mounted on the upper surface 254. Power is supplied to the pod 202a by an AC/DC adapter 266 through a pin and socket 265. Downloading of protocols to $E^2PROM$ 1408a or other information exchange is achieved via two additional contacts (not shown) or via the connector 265.

An override system is incorporated into the head 200a. A series of contacts 267 provides a similar method of sensing the presence of the body as the proximity sensor 716 described earlier. Multiple contacts 267 are spread along each side of the arrays of the diodes 210a outboard of the indicators 269. Contacts may be grouped in various patterns to create a pair of electrodes such as 718,720. Also two or more sets may be created, each with its own driver circuit. Thus, numerous contacts must be in contact with the body in order for the probe to activate. The contacts will be made from a metal to simulate the appearance of an LED. The contact 267 identify contact with the skin by varying the impedance in an a.c. circuit. The resultant frequency variations modulate a voltage signal in driver circuit 274 which is provided to the microprocessor 815*a*.

The flexible PCB 250 permits the head to accommodate curved surfaces and allows the head 200*a* to flex along both longitudinal and transverse axes for optimum engagement with the skin. To inhibit undue flexure of the control pod 202*a*, stiffening panels 275,276 are secured to the upper and lower layers 242,254. These may provide access to the electronic component or may be integrally molded with the layers 242,254. Conveniently, the panel 275 may incorporate the buttons 256,258,260 and switch 220 in a membrane switch panel. The simplified operation and control of the available protocols renders the unit suitable for home use without the intervention of a qualified practitioner. The incorporation of the override control, feedback look and diagnostic monitoring by the microprocessor provide the requisite level fo safely for such use.

The E$^2$PROM 1408*a* retains protocol instructions that can be accessed by the microprocessor 815*a* to reproduce the protocols. Other information retained in the E$^2$PROM may include identification allowing the GUI 105 to record patient history 23*a* as well as a measure of treatment compliance.

The embodiments of the invention in which an exclusive property or privilege is claimed are defined as follows:

1. A photon therapy unit having a treatment head including at least one photon emitter, a drive circuit to drive said photon emitting device, a control to modulate said drive circuit and a switch responsive to placement of said head on a treatment location, said switch inhibiting operation of said drive circuit until said emitter is placed on said treatment location and including at least one pair of terminals at spaced locations on said head and positioned relative to said photon emitting device to contact skin at said treatment location to complete an electrical circuit upon placement of said head on said treatment location with said emitter directed to said treatment location.

2. A photon therapy unit according to claim 1 wherein a photon emitting device is located between each of said pair of terminals.

3. A photon therapy unit according to claim 1 wherein said control is operable to override said drive circuit and to disable said emitters.

4. A photon therapy unit having a treatment head including at least one photon emitter; a drive circuit to drive said photon emitting device, a control to modulate said drive circuit and a switch responsive to placement of said head on a treatment location with said emitter directed to said treatment location, said switch inhibiting operation of said drive circuit until said emitter is placed on said treatment location and including an optical sensor responsive to ambient light to determine placement on said treatment location.

5. A photon therapy unit accordingly to claim 4 wherein said diagnostic function includes a microprocessor and an error signal is generated by said microprocessor.

6. A treatment head according to claim 5 wherein a backing is provided for said support, said backing being flexible and thermally conductive to secure said emitters on said support and thereby conduct heat from said emitters and away from said treatment area.

7. A treatment head according to claim 6 wherein said support is encapsulated by said thermally conductive backing.

8. A treatment head according to claim 5 wherein said backing has fins formed thereon to dissipate heat from said backing.

9. A treatment head according to claim 5 wherein a control circuit is located at one end of said head adjacent said array.

10. A treatment head according to claim 9 wherein a retaining bank is secured to said head at opposite ends of said array.

11. A treatment head according to claim 10 wherein one end of said retaining band is secured to said head adjacent to said array at said one end to inhibit flexure of said control circuit upon tightening of said retaining band.

12. A treatment head according to claim 9 wherein a control panel is provided at said one end on an opposite side thereof to said array.

13. A treatment head according to claim 12 wherein said support is flexible and said backing is molded from a thermally conductive material.

14. A photon therapy unit comprising a treatment head having at least one photon emitting device therein, and a drive circuit to drive said photon emitting device, a control unit to provide control signals to said drive circuit to implement one of a plurality of treatment protocols accessible to said unit and a graphical user interface to display a selection of said plurality of protocols to permit a user to select one of said treatment protocols from a plurality thereof, said protocols being presented on said graphical user interface as a representation of area to be treated.

15. A photon therapy unit according to claim 14 wherein said head includes an identification to advise said control unit of the characteristics of said head upon connection thereto.

16. A photon therapy unit according to claim 15 wherein said head includes a microprocessor to monitor operation of said head and communicate such operation to said control unit.

17. A photon therapy unit according to claim 14 wherein said graphical user interface includes a display of patient history.

18. A photon therapy unit according to claim 17 wherein said patient history is updated periodically from a memory associated with said head.

19. A photon therapy unit according to claim 14 wherein said graphical user interface includes a display of patient characteristics and selection of such characteristics adjusts a treatment protocol for a patient.

20. A treatment head for a photon therapy unit, said head having a plurality of discrete arrays of photon emitters, each having a support for said emitters to maintain said emitters in spaced relationship on a respective array, said arrays being arranged in seriatim and flexibly connected to one another to facilitate said head conforming to a treatment location.

21. A treatment head according to claim 20 wherein said arrays are connected by flexible tube extending between adjacent arrays, said tube containing electrical connections for each of said arrays.

22. A treatment head according to claim 21 wherein said tube forms a loop at an end opposite said one end for attachment of a retaining band.

23. A treatment head according to claim 20 wherein fins are formed on said head to dissipate heat from said emitters.

24. A treatment head according to claim 20 wherein a heat sink is positioned adjacent said support and said emitters are thermally connected to said heat sink by a moldable thermally conductive electrical insulator.

25. A treatment head according to claim 20 wherein said emitters are located in a thermally insulating plastics material arranged to be juxtaposed on a treatment location.

* * * * *